(12) United States Patent
Kudoh et al.

(10) Patent No.: US 7,202,069 B2
(45) Date of Patent: Apr. 10, 2007

(54) (R)-2-OCTANOL DEHYDROGENASES, METHODS FOR PRODUCING THE ENZYMES, DNA ENCODING THE ENZYMES, AND METHODS FOR PRODUCING ALCOHOLS USING THE ENZYMES

(75) Inventors: Masatake Kudoh, Ibaraki (JP); Hiroaki Yamamoto, Ibaraki (JP)

(73) Assignee: Daicel Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/766,421

(22) Filed: Jan. 27, 2004

(65) Prior Publication Data

US 2004/0126857 A1    Jul. 1, 2004

Related U.S. Application Data

(60) Division of application No. 09/978,758, filed on Oct. 16, 2001, now Pat. No. 6,706,507, which is a continuation-in-part of application No. PCT/JP01/01082, filed on Feb. 15, 2001.

(30) Foreign Application Priority Data

| Feb. 16, 2000 | (JP) | ............................ 2000-43506 |
| Dec. 8, 2000 | (JP) | ............................ 2000-374593 |

(51) Int. Cl.
| C12N 9/04 | (2006.01) |
| C12N 1/20 | (2006.01) |
| C12N 15/00 | (2006.01) |
| C12P 7/02 | (2006.01) |
| C12P 21/04 | (2006.01) |
| C12Q 1/00 | (2006.01) |
| C07H 21/04 | (2006.01) |

(52) U.S. Cl. .................. 435/190; 435/155; 435/252.3; 435/320.1; 435/440; 435/69.1; 435/71.1; 435/4; 435/26; 536/23.2; 536/23.74

(58) Field of Classification Search ............... 435/190, 435/155, 252.3, 320.1, 440, 69.1, 71.1, 4, 435/26; 536/23.2, 23.74

See application file for complete search history.

(56) References Cited

U.S. PATENT DOCUMENTS 5,126,256 A    6/1992    Ebeling et al. ............. 435/190

(Continued)

FOREIGN PATENT DOCUMENTS

JP    01-277494    * 11/1989

(Continued)

OTHER PUBLICATIONS

ChemExper Catalog. 2-Acetonyloxy-3,4-Difluoronitrobenzene.*

(Continued)

Primary Examiner—P. Achutamurthy
Assistant Examiner—Yong D. Pak
(74) Attorney, Agent, or Firm—Fish & Richardson P.C.

(57) ABSTRACT

This invention provides (R)-2-octanol dehydrogenase that catalyzes oxidation-reduction reaction using $NAD^+$ (NADH) as a coenzyme and the genes that encodes them. The enzymes of this invention can be obtained from microorganisms such as the genera *Pichia, Candida*, and *Ogataea*, and so on. It is possible to produce alcohols, in particular, alcohols such as (S)-4-halo-3-hydroxybutyric acid esters and (R)-propoxybenzene derivatives by reducing ketones with this (R)-2-octanol dehydrogenase. Moreover, the (R)-2-octanol dehydrogenase of this invention is excellent in activity and stereoselectivity.

22 Claims, 11 Drawing Sheets

U.S. PATENT DOCUMENTS

| | | | |
|---|---|---|---|
| 5,385,833 | A | 1/1995 | Bradshaw et al. |
| 6,218,156 | B1 | 4/2001 | Yasohara et al. |
| 2003/0054520 | A1* | 3/2003 | Bommanus et al. ........ 435/190 |

FOREIGN PATENT DOCUMENTS

| | | |
|---|---|---|
| JP | 1281092 | 11/1989 |
| JP | 2000-236883 | 5/2000 |
| WO | WO 01/05996 A1 | 1/2001 |

OTHER PUBLICATIONS

Mitamura T. et al., "Structure of Isozyme Genes of Glucose Dehydrogenase from *Bacillus megaterium* IAM1030", Journal of Fermentation and Bioengineering, vol. 70(6), pp. 363-369 (1990).

Peters J. et al., "A novel NADH-dependent carbonyl reductase with an extremely broad substrate range from *Candida parpsilosis*: Purification and characterization", Enzyme Microb. Technol., vol. 15(11), pp. 950-958 (1993).

Ueda M. et al., "Long-Chain Alcohol Dehydrogenase of *Candida* Yeast", Methods in Enzymology, vol. 188, pp. 171-175 (1990).

Sudovtsov VE, "The Study of the Activity of Alcohol Dehydrogenase From the Cytoplasm of Some Yeasts", Prikl Biokhim Mikrobiol, vol. 27(1), pp. 61-67 (1991) (English Summary at p. 67).

Luque T. et al., "Structure of the *Drosphila melanogaster* glutathione-dependent formaldehyde dehydrogenase/octanol dehydrogenase gene (class III alcohol dehydrogenase)", Eur. J. Biochem., vol. 225(3), pp. 985-993 (1994).

Murdanoto AP. et al., "Purification and Properties of Methyl Formate Synthase, a Mitochondrial Alcohol Dehydrogenase, Participating in Formaldehyde Oxidation in Methylotropnic Yeasts", Applied and Environmental Microbiology, vol. 63(5), pp. 1715-1720 (1997).

Patel et al., "Microbial production of methylketones: properties of purified yeast secondary alcohol dehydrogenase" J. of Applie Biochemistry, vol. 3, pp. 218-232, 1981.

Bradshaw et al., "A New Alcohol Dehydrogenase with Unique Stereospecificity from *Pseudomonas* sp.", Bioorganic Chem., 19:398-417, 1991.

Zelinski et al., "Purification and characterization of a novel carbonyl reductase isolted from *Rhodococcus erythropolis*", J. of Biotech., 33:283-292, 1994.

* cited by examiner

(R)-2-OCTANOL DEHYDROGENASES, METHODS FOR PRODUCING THE ENZYMES, DNA ENCODING THE ENZYMES, AND METHODS FOR PRODUCING ALCOHOLS USING THE ENZYMES

CROSS REFERENCE TO RELATED APPLICATION

This application is a divisional (and claims the benefit of priority under 35 USC 120) of U.S. application Ser. No. 09/978,758, filed Oct. 16, 2001, now U.S. Pat. No. 6,706, 507, which claims priority to and is a continuation-in-part of PCT/JP01/01082, filed Feb. 15, 2001, which claims priority from Japanese Application 2000-43506, filed Feb. 16, 2000, and Japanese application No. 2000-374593, filed Dec. 8, 2000. The disclosures of the prior applications are considered part of (and are incorporated herein by reference in their entirety) the disclosure of this application.

TECHNICAL FIELD

The present invention relates to novel (R)-2-octanol dehydrogenases useful for producing alcohols, ketones, particularly for producing optically active alcohols such as (S)-4-halo-3-hydroxybutyric acid esters and (R)-propoxybenzene derivatives, DNAs encoding the enzyme, methods for producing the enzymes, and methods for producing alcohols, ketones, particularly for producing optically active alcohols such as (S)-4-halo-3-hydroxybutyric acid esters and (R)-propoxybenzene derivatives using the enzymes.

BACKGROUND (S)-4-halo-3-hydroxybutyric acid esters are compounds used as intermediates in synthesizing HMG-CoA reductase inhibitors, D-carnitine, etc. These compounds are useful for syntheses of medicines and pesticides. Especially, how to get (to synthesize or separate) optically pure enantiomers of (S)-4-halo-3-hydroxybutyric acid esters is industrially important problem. So far, asymmetric synthesis, crystallization, and asymmetric reduction method using microorganisms such as baker's yeast (Unexamined Published Japanese Patent Application (JP-A) Sho 61-146191, JP-A Hei 6-209782, and such) are known as methods for producing (S)-4-halo-3-hydroxybutyric acid esters. However, these known methods are inappropriate for industrial use because of the problems such as low optical purities of products, low yield, etc.

In addition, enzymes that reduce 4-haloacetoacetic acid esters to (S)-4-halo-3-hydroxybutyric acid esters are also being searched. For example, enzymes indicated below are known. The methods for synthesizing (S)-4-halo-3-hydroxybutyric acid esters using these enzymes are reported. These enzymes are, however, reductases that use reduced form of nicotinamide adenine dinucleotide phosphate (NADPH) as a coenzyme. Therefore, synthesizing (S)-4-halo-3-hydroxybutyric acid esters using these enzymes requires addition and regeneration of NADPH, which is expensive and chemically unstable, and is industrially disadvantageous.

Some reductases derived from baker's yeast (D-enzyme-1, D-enzyme-2, J. Am. Chem. Soc., 107:2993–2994, 1985)

Aldehyde reductase 2 derived from *Sporobolomyces salmonicolor* (Appl. Environ. Microbiol., 65:5207–5211, 1999)

Keto pantothenic acid ester reductase derived from *Candida macedoniensis* (Arch. Biochem. Biophys., 294: 469–474, 1992)

4-Chloroacetoacetic acid ethyl ester reductase derived from *Geotrichum candidum* (Enzyme Microb. Technol. 14, 731–738, 1992)

Carbonyl reductase derived from *Candida magnoliae* (WO 98/35025)

Carbonyl reductase derived from *Kluyveromyces lactis* (JP-A Hei 11-187869)

β-Ketoacyl-acyl carrier protein reductase as one of fatty acid synthases type II (JP-A 2000-189170)

Although 3α-hydroxysteroid dehydrogenase (JP-A Hei 1-277494), glycerol dehydrogenase (Tetrahedron Lett. 29, 2453–2454, 1988), and alcohol dehydrogenase derived from *Pseudomonas sp.* PED (J. Org. Chem., 57:1526–1532, 1992) are known as reductases using reduced form of nicotinamide adenine dinucleotide (NADH) as a electron donor, these enzymes are industrially disadvantageous because the activity of reaction for synthesizing (S)-4-halo-3-hydroxybutyric acid esters is low.

As indicated above, known methods for producing (S)-4-halo-3-hydroxybutyric acid esters using microorganisms and enzymes were not satisfactory in some respects such as optical purities, yields, activities, etc. These problems have made known methods difficult for industrial use.

On the other hand, (R)-propoxybenzene derivatives (JP-A Hei 02-732) are useful compounds as intermediates in synthesizing medicines, especially, optically active substances of ofloxacin ((S)-(−)-9-fluoro-3-methyl-10-(4-methyl-1-piperazinyl)-7-oxo-2,3-dihydro-7H-pyrido[1,2,3-de] [1,4]benzooxazine-6-carboxylic acid, JP-A Sho 62-252790), which is synthetic antibacterial drugs. How to get (to synthesize or separate) optically pure enantiomers of these compounds is industrially important problem.

Asymmetric acylation of racemates of propoxybenzene derivatives using lipase and esterase (JP-A Hei 03-183489) is known as a method for producing (R)-propoxybenzene derivatives. In this method, a process to separate remaining raw materials and acylated products after acylation of (R) form and a process to deacylate the acylated products are required. Therefore, this known method is inappropriate for industrial use because these processes are complicated.

The method for asymmetric reduction of acetonyloxybenzene derivatives using microorganisms has been also reported. However, this known method is inappropriate for industrial use because optical purities of (R)-propoxybenzene derivatives produced is as low as 84 to 98% (JP-A Hei 03-183489) or 8.8 to 88.4% (JP-A Hei 05-68577) and because the concentration of substrate is also as low as 0.1 to 0.5%. As the method in which high optical purities can be obtained by asymmetric reduction, the method using carbonyl reductase produced by *Candida magnoliae* (JP-A 2000-175693) was reported to synthesize (R)-propoxybenzene derivatives whose optical purities are 99% or more. However, this carbonyl reductase uses NADPH as a coenzyme. Therefore, synthesizing (R)-propoxybenzene derivatives using this enzyme requires addition and regeneration of NADPH, which is expensive and chemically unstable, and is industrially disadvantageous.

SUMMARY

An objective of the present invention is to provide novel enzymes that can reduce 4-haloacetoacetic acid esters using NADH as a coenzyme and produce (S)-4-halo-3-hydroxybutyric acid esters having high optical purities. Furthermore, an objective of the present invention is to provide methods for producing, using the enzyme, (S)-4-halo-3-hydroxybutyric acid esters having high optical purities.

In addition, an objective of the present invention is to provide novel enzymes that can produce optically highly pure (R)-propoxybenzene derivatives, which are useful as intermediates in synthesizing antibacterial drugs, using NADH as a coenzyme. Furthermore, an objective of the present invention is to provide methods for producing, using the enzyme, (R)-propoxybenzene derivatives that have high optical purities.

The present inventors thought that alcohol dehydrogenase that can use NADH as an electron donor was useful for industrial use. NADH is cheaper and chemically more stable than NADPH. To discover enzymes that can effectively produce optically active (S)-4-halo-3-hydroxybutyric acid esters, the present inventors screened for alcohol dehydrogenase which has high activity on (R)-2-octanol, which has the same configuration as that of (S)-4-halo-3-hydroxybutyric acid esters and which has long chain as long as that of 4-haloacetoacetic acid esters.

Previous findings reported the enzymes derived from *Comamonas terrigena*, *Pichia* sp. NRRL-Y-11328, and *pseudomonas* sp. SPD6 as secondary alcohol dehydrogenases that can oxidize (R)-2-octanol stereoselectively and have activities to produce 2-octanone. However, no report has been made that these enzymes can reduce 4-haloacetoacetic acid esters and produce (S)-4-halo-3-hydroxybutyric acid esters. Activities to produce (S)-4-halo-3-hydroxybutyric acid esters by reducing 4-haloacetoacetic acid esters whose carbonyl group is bound to bulky side chains are expected to be low because activities of these enzymes for (R)-2-octanol are not significantly higher than activities for secondary alcohol like 2-propanol, which has short side chains.

Therefore, the present inventors screened widely for microorganisms that possess enzymes having ability to oxidize (R)-2-octanol preferentially. As a result, they have discovered that the microorganisms belonging to the genera below possess enzymes having ability to oxidize (R)-2-octanol preferentially:

Genus *Pichia*
Genus *Candida*
Genus *Ogataea*

Specifically, microorganisms below are found to possess enzymes having ability to oxidize (R)-2-octanol preferentially.

*Pichia finlandica*
*Pichia jadinii*
*Candida utilis*
*Ogataea wickerhamii*

Moreover, the present inventors cultivated these microorganisms and purified enzymes that can oxidize (R)-2-octanol from the microorganisms. As a result of examination of properties of these enzymes, the enzymes were found to oxidize (R)-2-octanol highly stereoselectively and, furthermore, to oxidize many secondary alcohols other than (R)-2-octanol stereoselectively. The enzymes were also found not only to possess high activities to reduce 4-chloroacetoacetic acid ethyl ester and to produce (S)-4-chloro-3-hydroxybutyric acid esters but also to possess high activities to reduce 2-acetonyloxy-3,4-difluoronitrobenzene and produce 2,3-difluoro-6-nitro[[(R)-2-hydroxypropyl]oxy]benzene. Thus, the inventions were completed.

Specifically, the present invention relates to novel (R)-2-octanol dehydrogenase useful for producing alcohols, ketones, particularly for producing optically active alcohols such as (S)-4-halo-3-hydroxybutyric acid esters, DNA encoding the enzyme, methods for producing the enzyme, and methods for producing alcohols, ketones, particularly for producing optically active alcohols such as (S)-4-halo-3-hydroxybutyric acid esters and (R)-propoxybenzene derivatives using the enzyme.

[1] An (R)-2-octanol dehydrogenase having the following physicochemical properties (1) and (2):
  (1) Action
    i) The enzyme produces ketone by oxidizing alcohol using oxidized form of β-nicotinamide adenine dinucleotide as a coenzyme, and
    ii) The enzyme produces alcohol by reducing ketone using reduced form of β-nicotinamide adenine dinucleotide as a coenzyme, and
  (2) Substrate specificity
    i) The enzyme preferentially oxidizes (R)-2-octanol of two optical isomers of 2-octanol, and
    ii) The enzyme produces (S)-4-halo-3-hydroxybutyric acid esters by reducing 4-haloacetoacetic acid esters.

[2] The (R)-2-octanol dehydrogenase of [1] having the following physicochemical properties (3) and (4):
  (3) Optimum pH
    Optimum pH for the oxidation reaction ranges from 8.0 to 11.0, and that for the reduction ranges from 5.0 to 6.5, and
  (4) Substrate specificity
    i) The enzyme shows higher activity on secondary alcohols than on primary alcohols, and
    ii) The enzyme shows significantly higher activity on (R)-2-octanol than on 2-propanol.

[3] The (R)-2-octanol dehydrogenase of [1] or [2], wherein the (R)-2-octanol dehydrogenase is derived from a microorganism selected from the group consisting of the genus *Pichia*, genus *Candida*, and genus *Ogataea*.

[4] The (R)-2-octanol dehydrogenase of [3], wherein the microorganism belonging to the genus *Pichia* is *Pichia finlandica*.

[5] The (R)-2-octanol dehydrogenase of [3], wherein the microorganism belonging to the genus *Pichia* is *Pichia jadinii*.

[6] The (R)-2-octanol dehydrogenase of [3], wherein the microorganism belonging to the genus *Candida* is *Candida utilis*.

[7] The (R)-2-octanol dehydrogenase of [3], wherein the microorganism belonging to the genus *Ogataea* is *Ogataea wickerhamii*.

[8] A method for producing the (R)-2-octanol dehydrogenase of [1] or [2], the method comprising cultivating a microorganism selected from the group consisting of the genus *Pichia*, genus *Candida*, and the genus *Ogataea*, the microorganism producing the enzyme of [1] or [2].

[9] An isolated polynucleotide of (a) to (e) below, the polynucleotide encoding a protein having activity of (R)-2-octanol dehydrogenase:
  (a) a polynucleotide comprising the nucleotide sequence of SEQ ID NO:1,
  (b) a polynucleotide encoding a protein comprising the amino acid sequence of SEQ ID NO:2,
  (c) a polynucleotide encoding a protein comprising the amino acid sequence of SEQ ID NO:2 in which one or more amino acids are replaced, deleted, inserted, and/or added,
  (d) a polynucleotide hybridizing under stringent conditions with a polynucleotide comprising the nucleotide sequence of SEQ ID NO:1, and (e) a polynucleotide encoding an amino acid sequence having not less than 70% homology to the amino acid sequence of SEQ ID NO:2.

As used herein, an "isolated polynucleotide" is a polynucleotide, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated polynucleotide which is longer than or equivalent in length to the reference sequence, e.g., SEQ ID NO:1, the comparison is made with the full length of the reference sequence. Where the isolated polynucleotide is shorter that the reference sequence, e.g., shorter than SEQ ID NO:1, the comparison is made to a segment of the reference sequence of the same length (excluding any loop required by the homology calculation).

[10] A substantially pure protein encoded by the polynucleotide of [9].

The term "substantially pure" as used herein in reference to a given protein or polypeptide means that the protein or polypeptide is substantially free from other biological macromolecules. For example, the substantially pure protein or polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

[11] A recombinant vector into which the polynucleotide of [9] is inserted.

[12] The recombinant vector of [11], wherein a polynucleotide encoding a dehydrogenase that can catalyze oxidation-reduction reaction using β-nicotinamide adenine dinucleotide as a coenzyme is further inserted.

[13] A transformant comprising the polynucleotide of [9] or the vector of [11] in an expressible manner.

[14] A method for producing the protein of [10], the method comprising cultivating the transformant of [13].

[15] A method for producing a alcohol, the method comprising reacting the (R)-2-octanol dehydrogenase of [1] or [2], the protein of [10], a microorganism producing the enzyme or the protein, or a processed product of the microorganism with a ketone to reduce the ketone.

[16] The method of [15], wherein the microorganism is the transformant of [13].

[17] The method of [15], wherein the ketone is a 4-haloacetoacetic acid ester derivative and wherein the alcohol is an (S)-4-halo-3-hydroxybutyric acid ester derivative.

[18] The method of [17], wherein the 4-haloacetoacetic acid ester derivative is 4-chloroacetoacetic acid ethyl ester and wherein the alcohol is (S)-4-chloro-3-hydroxybutyric acid ethyl ester.

[19] The method of [15], wherein the ketone is an acetonyloxybenzene derivative represented by the generic formula 1:

Generic Formula 1

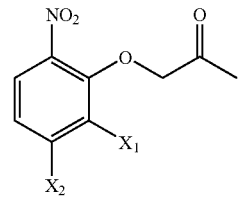

where each of x1 and x2 indicates a halogen atom; and wherein the alcohol is a propoxybenzene derivative represented by the generic formula 2:

Generic Formula 2

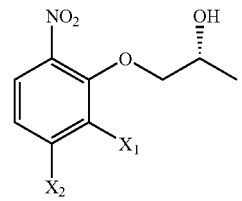

[20] The method of [19], wherein the acetonyloxybenzene derivative is 2-acetonyloxy-3,4-difluoronitrobenzene and wherein the alcohol is 2,3-difluoro-6-nitro[[(R)-2-hydroxypropyl]oxy]benzene.

[21] The method of [15], the method further additionally comprising converting oxidized form of β-nicotinamide adenine dinucleotide into reduced form thereof.

[22] A method for producing a ketone, the method comprising reacting the (R)-2-octanol dehydrogenase of [1] or [2], the protein of [10], a microorganism producing the enzyme or the protein, or a processed product of the microorganism with an alcohol to oxidize the alcohol.

[23] A method for producing an optically active alcohol, the method comprising the steps of reacting the (R)-2-octanol dehydrogenase of [1] or [2], the protein of [10], a microorganism producing the enzymes or the protein, or a processed product of the microorganism with a racemic alcohol to preferentially oxidize either optical isomer, and obtaining the remaining optically active alcohol.

[24] The method of [22] or [23], the method further additionally comprising converting reduced form of β-nicotinamide adenine dinucleotide into oxidized form thereof.

The present invention provides enzymes having the following physicochemical properties (1) and (2):

(1) Action
  i) The enzyme produces ketone by oxidizing alcohol using oxidized form of β-nicotinamide adenine dinucleotide ($NAD^+$) as a coenzyme, and
  ii) The enzyme produces alcohol by reducing ketone using reduced form of β-nicotinamide adenine dinucleotide (NADH) as a coenzyme, and
(2) Substrate Specificity
  i) The enzyme preferentially oxidizes (R)-2-octanol of two optical isomers of 2-octanol, and
  ii) The enzyme produces (S)-4-halo-3-hydroxybutyric acid esters by reducing 4-haloacetoacetic acid esters.

Preferably, the enzymes of the present invention further have the following enzymatic properties (3) and (4):
(3) Optimum pH
  Optimum pH for the oxidation reaction ranges from 8.0 to 11.0, and that for the reduction ranges from 5.0 to 6.5, and
(4) Substrate specificity
  i) The enzyme shows higher activity on secondary alcohols than on primary alcohols, and
  ii) The enzyme shows significantly higher activity on (R)-2-octanol than on 2-propanol.

Furthermore, preferable (R)-2-octanol dehydrogenases in this invention have the following physicochemical and enzymatic properties (5) to (8):
(5) Optimum working temperature range
  The optimum temperature for the oxidation reaction of (R)-2-octanol ranges from 45° C. to 55° C. The optimum temperature for the reduction reaction of ethyl 4-chloroacetoacetate ranges from 55° C. to 60° C.
(6) Stable pH range
  The enzyme is stable in the range of pH 8 to 9.
(7) Inhibition
  The enzyme is slightly inhibited by mercury chloride and chelating agent ethylenediaminetetraacetic acid disodium salt (EDTA·2Na).
(8) Stabilization
  The enzyme is stabilized by N-ethylmaleimide, o-phenanthroline, magnesium chloride, calcium chloride, and manganese chloride.
(9) Purification method
  The enzyme of the present invention can be purified by usual purification methods from microorganisms producing the enzyme. For example, the enzyme can be purified by carrying out protamine sulfate precipitation after disrupting fungal bodies, by salting-out the centrifugal supernatant with ammonium sulfate, and further by combining anion-exchange chromatography, hydrophobic chromatography, affinity chromatography, gel filtration, etc.

The term "dehydrogenase" used herein means an enzyme that catalyzes dehydrogenation, that is, oxidation reaction in which hydrogens are removed from a compound including hydrogens. Furthermore, the enzyme possesses reduction activity on ketone and can catalyze reverse reaction of oxidation reaction under reductive conditions. Therefore, "dehydrogenase" in this invention possesses activity catalyzing reduction reaction that is reverse reaction of the oxidation reaction and in which hydrogens are added. In general, when possessing the same activities, enzymes called "dehydrogenase", "oxidation-reduction enzyme", "oxidase", "reductase", or the like are included in the "dehydrogenase" of this invention.

In the present invention, reduction activity on 4-chloroacetoacetic acid ester can be measured as follows. The activity can be validated by incubating at 30° C. the reaction mixture containing potassium phosphate buffer (pH 6.5, 100 mM), 0.2 mM NADH, 20 mM ethyl 4-chloroacetoacetate, and the enzyme and by measuring decrease of absorbance at 340 nm accompanying decrease of NADH. 1 U was defined as the amount of the enzyme catalyzing decrease of 1 µmol of NADH for 1 minute. Quantification of proteins can be done by dye binding method using the protein assay kit (BIORAD).

On the other hand, oxidation activity on (R)-2-octanol can be measured as follows. The activity can be validated by incubating at 30° C. the reaction mixture containing Tris-HCl buffer (pH 8.5, 50 mM), 2.5 mM $NAD^+$, 5 mM (R)-2-octanol, and the enzyme and by measuring increase of absorbance at 340 nm accompanying generation of NADH. 1 U was defined as the amount of the enzyme catalyzing generation of 1 µmol of NADH for 1 minute.

(R)-2-octanol dehydrogenase of this invention has high oxidation activity on (R)-2-octanol. In addition, the oxidation activity on (R)-2-octanol of the enzyme is significantly higher than that on 2-propanol. Herein, when the rate of change in absorbance at 340 nm accompanying increase or decrease of NADH per unit time in contacting with (R)-2-octanol as a substance in the presence of $NAD^+$ is twice or more and preferably five times or more larger as relative activity when taking the rate for 2-propanol as 1, it can be said that the dehydrogenase activity is significantly higher.

In this invention, that (R)-2-octanol dehydrogenase "preferentially" oxidizes (R)-2-octanol means that the enzymatic activity of (R)-2-octanol dehydrogenase on S form is 50 or less, preferably 20 or less, and more preferably 10 or less when taking the activity on R form as 100.

(R)-2-octanol dehydrogenases having physicochemical properties as mentioned above can be obtained from culture of microorganisms producing this enzyme. For example, strains producing the enzyme of this invention can be found in the yeast of the genus *Pichia*, the genus *Candida*, and the genus *Ogataea*. Especially, *Pichia finlandica* and *Pichia jadinii* as the genus *Pichia*, *Candida utilis* as the genus *Candida*, and *Ogataea wickerhamii* as the genus *Ogataea* are excellent in ability to produce (R)-2-octanol dehydrogenase of this invention. Examples of strains available for obtaining the (R)-2-octanol dehydrogenase of this invention are as follows:
  (i) *Pichia finlandica*: DSM 70280, DSM 1380
  (ii) *Pichia jadinii*: DSM 2361, DSM 70167, IFO 0987
  (iii) *Candida utilis*: IFO 0988, IFO 0626
  (iv) *Ogataea wickerhamii*: IFO 1706

As for secondary alcohol dehydrogenase produced by *Pichia finlandica*, there is a report that showed 2-propanol dehydrogenase activity using cell-free extract (Biochimica et Biophysica Acta, 716:298–307, 1982). However, according to the additional test by the inventors, multiple 2-propanol dehydrogenases were included in the cell-free extract of this strain. On the other hand, the (R)-2-octanol dehydrogenase of this invention is a minor component having very weak 2-propanol dehydrogenase activity. Therefore, the (R)-2-octanol dehydrogenase of this invention is distinctly different from the enzymes describe in this reference.

The microorganisms mentioned above are cultivated in a general medium used for cultivation of fungi such as YM medium. The desired enzymes can be well obtained especially from *Pichia finlandica* using either of glucose, glycerol, or methanol as carbon source in the medium. The desired enzymes can be well obtained from *Candida utilis* using, in particular, methanol as carbon source in the culture medium. Fungus bodies are recovered after enough proliferation and disrupted in a buffer to which reducing agents like 2-mercaptoethanol and such and protease inhibitors like phenylmethansulfonyl fluoride PMFS are added to make cell-free extract. The enzyme can be purified from cell-free extract by combining fractionation of proteins based on their solubility, various chromatographies, etc. As methods for fractionation of proteins based on their solubility, for example, precipitation with organic solvent such as acetone or dimethylsulfoxide, salting out with ammonium sulfate, or the like can be used. On the other hand, as chromatographies, cation exchange chromatography, anion exchange chromatography, gel filtration, hydrophobic chromatography, and many affinity chromatographies using chelates, pigments, antibodies, and such are known. More specifically, through hydrophobic chromatography with Phenyl-Toyopearl, anion exchange chromatography with DEAE-Sepharose, hydrophobic chromatography with Butyl-Toyopearl, affinity chromatography with Blue-Sepharose, gel filtration with Superdex 200, and such, the enzyme can be purified to electrophoretically almost single band.

The present invention relates to polynucleotides encoding (R)-2-octanol dehydrogenases and their homologues. In this invention, polynucleotides can be naturally existing polynucleotides such as DNAs or RNAs and can be also polynucleotides including artificially synthesized nucleotide derivatives.

The polynucleotide encoding the (R)-2-octanol dehydrogenase of the present invention comprises, for example, the nucleotide sequence of SEQ ID NO:1. The nucleotide sequence of SEQ ID NO:1 encodes a polypeptide comprising the amino acid sequence of SEQ ID NO:2. The polypeptide comprising this amino acid sequence constitutes preferred embodiments of the (R)-2-octanol dehydrogenase of the present invention.

The polynucleotide of the present invention includes a polynucleotide encoding a polypeptide having above-mentioned physicochemical properties (1) and (2) as well as comprising the amino acid sequence of SEQ ID NO:2 in which one or more amino acids are deleted, substituted, inserted, and/or added. One skilled in the art can properly introduce substitution, deletion, insertion, and/or addition mutation into the DNA comprising the nucleotide sequence of SEQ ID NO:1 by site-specific mutagenesis (Nucleic Acid Res., 10:6487, 1982: Methods in Enzymol., 100:448, 1983; Molecular Cloning 2nd Ed., Cold Spring Harbor Laboratory Press (1989), PCR: A Practical Approach, IRL Press, pp. 200 (1991)).

The number of amino acids that are mutated is not particularly restricted, as long as the (R)-2-octanol dehydrogenase activity is maintained. Normally, it is within 50 amino acids, preferably within 30 amino acids, more preferably within 10 amino acids, and even more preferably within 3 amino acids. The site of mutation may be any site, as long as the (R)-2-octanol dehydrogenase activity is maintained. An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, aspargine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In addition, the polynucleotide of the present invention includes polynucleotides hybridizing under stringent conditions to the DNA comprising the nucleotide sequence of SEQ ID NO:1 as well as encoding a protein having above-mentioned physicochemical properties (1) and (2). The "polynucleotide hybridizing under stringent conditions" means a polynucleotide hybridizing to a probe nucleotide that has one or more segments of at least 20 consecutive nucleotides, preferably at least 30 consecutive nucleotides, for example, 40, 60, or 100 consecutive nucleotides, arbitrarily selected from the sequence in the nucleotide sequence shown in SEQ ID NO:1, by using, for example, ECL Direct Nucleic Acid Labeling and Detection System (Amersham-Pharmacia Biotech) under conditions recommended in the attached manual (washing with the primary wash buffer containing 0.5×SSC at 42° C.).

Also included in the invention is a polynucleotide that hybridizes under high stringency conditions to the nucleotide sequence of SEQ ID NO:1 or a segment thereof as described herein. "High stringency conditions" refers to hybridization in 6×SSC at about 45° C., followed by one or more washes in 0.2×SSC, 0.1% SDS at 65° C.

Polynucleotides that can hybridize with DNA comprising the nucleotide sequence of SEQ ID NO:1 under stringent conditions include those comprising nucleotide sequences similar to SEQ ID NO:1. It is highly possible that such polynucleotides encode proteins functionally equivalent to the protein comprising the amino acid sequence of SEQ ID NO:2.

Furthermore, the polynucleotide of the present invention includes a polynucleotide encoding a protein exhibiting percent identity of at least 70%, preferably at least 80% or 90%, more preferably 95% or more to the amino acid sequence of SEQ ID NO:2. As used herein, "percent identity" of two amino acid sequences, or of two nucleic acid sequences, is determined using the algorithm of Karlin and Altschul (PNAS USA, 87:2264–2268, 1990), modified as in Karlin and Altschul, PNAS USA, 90:5873–5877, 1993). Such an algorithm is incorporated into the NBLAST and XBLAST programs of Altschul et al. (J. Mol. Biol., 215: 403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res., 25:3389–3402, 1997). When utilizing BLAST and Gapped-BLAST programs the default parameters of the respective programs (e.g., XBLAST and NBLAST) are used to obtain nucleotide sequences homologous to a nucleic acid molecule of the invention. Homology search of protein can readily be performed, for example, on the Internet, for example, in databases related to amino acid sequences of protein, such as SWISS-PROT, PIR, and such; databases related to DNAs, such as DNA Databank of JAPAN (DDBJ), EMBL, GenBank, and such; databases related to deduced amino acid sequences based on DNA sequences; and such by using the FASTA program, BLAST program, etc. As a result of homology search in SWISS-PROT using BLAST program and amino acid sequence of SEQ ID NO:2, the protein that showed the highest homology among known proteins was glucose dehydrogenase of *Bacillus subtilis* which showed 43% identity and 61% Positives. Not less than 70% homology in this invention indicates, for example, the value of homology in Positive using BLAST program.

In this invention, a polynucleotide encoding a protein having the physicochemical properties (1) and (2) above is especially called "homologue" to a polynucleotide comprising the nucleotide sequence of SEQ ID NO:1. Homologues can be isolated by PCR cloning and hybridization from other organisms based on the nucleotide sequence of SEQ ID NO:1, in addition to by mutation introduction. For example, the nucleotide sequence of SEQ ID NO:1 is that of the gene isolated from *Pichia finlandica*. Besides, a polynucleotide encoding a protein that has the physicochemical properties (1) and (2) above and that can be obtained from a microorganism such as *Pichia jadinii, Candida utilis* as a yeast belonging to the genus *Candida, Ogataea wickerhamii* as a yeast belonging to the genus *Ogataea*, and so on is included in this invention.

The polynucleotides of this invention are useful for genetic engineering production of the (R)-2-octanol dehydrogenase of this invention. Alternatively, microorganisms having (R)-2-octanol dehydrogenase activity that is useful for producing ketones and alcohols can be produced by genetic engineering using the polynucleotides of this invention.

The present invention encompasses an (R)-2-octanol dehydrogenase having the amino acid sequence of SEQ ID NO:2 and having above-mentioned physicochemical properties (1) and (2) as well as homologues thereof. The protein comprising the amino acid sequence of SEQ ID NO:2 constitutes preferred embodiments of the (R)-2-octanol dehydrogenase of the present invention.

The homologue of the (R)-2-octanol dehydrogenase of the present invention comprises the amino acid sequence of SEQ ID NO:2 in which one or more amino acids are deleted, substituted, inserted, and/or added. One skilled in the art can readily obtain a DNA encoding such a homologue of the (R)-2-octanol dehydrogenase by properly introducing substitution, deletion, insertion, and/or addition mutation into the DNA comprising the nucleotide sequence of SEQ ID NO:1 by site-specific mutagenesis (Nucleic Acid Res., 10:6487, 1982; Methods in Enzymol., 100:448, 1983; Molecular Cloning 2nd Ed., Cold Spring Harbor Laboratory Press (1989), PCR: A Practical Approach IRL Press pp. 200 (1991)) or the like. The homologue of the (R)-2-octanol dehydrogenase of SEQ ID NO:2 is available by introducing into a host a DNA encoding the homologue of the (R)-2-octanol dehydrogenase and expressing it in the host.

Furthermore, the homologue of the (R)-2-octanol dehydrogenase of the present invention includes a protein exhibiting percent identity of at least 70%, preferably at least 80% or 90%, more preferably 95% or more to the amino acid sequence of SEQ ID NO:2. Homology search of protein can readily be performed, for example, on the Internet, for example, in databases related to amino acid sequences of protein, such as SWISS-PROT, PIR, and such; databases related to DNAs, such as DNA Databank of JAPAN (SWISS-PROT), EMBL, GenBank, and such; databases related to deduced amino acid sequences based on DNA sequences; and such by using the FASTA program, BLAST program, etc. As a result of homology search in SWISS-PROT using BLAST program and amino acid sequence of SEQ ID NO:2, the protein that showed the highest homology among known proteins was glucose dehydrogenase of *Bacillus subtilis* which showed 43% identity and 61% Positives. Not less than 70% homology in this invention indicates, for example, the value of homology in Positive using BLAST program.

The DNA encoding the (R)-2-octanol dehydrogenase of the present invention may be isolated, for example, by using the following procedure.

After purification of the enzyme of this invention, multiple amino acid sequences can be determined by analyzing N-terminal amino acid sequences, and further, by cleaving the protein using enzymes such as lysyl endopeptidase, V8 protease, and such, by purifying peptide fragments by reverse-phase liquid chromatography and such, and by analyzing amino acid sequence with protein sequencer.

If partial amino acid sequences are revealed, nucleotide sequences encoding the amino acid sequences can be inferred. The DNA fragment of this invention can be obtained by PCR by designing primers for PCR based on the inferred nucleotide sequences or the nucleotide sequence of SEQ ID NO:1 and by using chromosomal DNA or cDNA library of the enzyme-producing strain as a template.

Furthermore, using the obtained DNA fragment as a probe, the DNA of this invention can be obtained by colony or plaque hybridization using a library obtained by transforming *E. coli* with a phage or plasmid into which restriction enzyme digestion products of the chromosomal DNA of the enzyme-producing strain are introduced or a cDNA library.

In addition, the DNA of the present invention can be obtained by analyzing the nucleotide sequence of the DNA fragment obtained by PCR, by designing PCR primers, based on the sequence already obtained, to extend the DNA outward, by digesting, with an appropriate restriction enzyme(s), the chromosomal DNA of the strain producing the enzyme of interest and then, by performing inverse PCR (Genetics, 120:621–623, 1988) using the self-ligated circular DNA as a template; or alternatively by using RACE method (Rapid Amplification of cDNA End; "Experimental manual for PCR" pp. 25–33, HBJ Press).

The DNA of the present invention includes not only the genomic DNA and cDNA cloned by the above-mentioned methods but also chemically synthesized DNA.

The thus-isolated DNA encoding the (R)-2-octanol dehydrogenase of the present invention is inserted into a known expression vector to provide a (R)-2-octanol dehydrogenase-expressing vector. Further, by culturing cells transformed with the expression vector, the (R)-2-octanol dehydrogenase of the present invention can be obtained from the transformed cells.

In the present invention, there is no restriction on the microorganism to be transformed for expressing (R)-2-octanol dehydrogenase whose coenzyme is $NAD^+$, as long as the organism is capable of being transformed with the vector containing the DNA encoding the polypeptide with activity of (R)-2-octanol dehydrogenase whose coenzyme is $NAD^+$ and capable of expressing activity of (R)-2-octanol dehydrogenase whose coenzyme is $NAD^+$. Available microorganisms are those for which host-vector systems are available and include, for example:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus;* actinomycetes such as the genus *Rhodococcus* and the genus *Streptomyces;* yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida;* and fungi such as the genus *Neurospora*, the genus *Aspergillus*, the genus *Cephalosporium*, and the genus *Trichoderma*; etc.

Procedure for preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express, in a microorganism, the gene encoding the (R)-2-octanol dehydrogenase of the present invention whose coenzyme is $NAD^+$, it is necessary to introduce the DNA into a plasmid vector or phage vector that is stable in the microorganism and to let the genetic information transcribed and translated. To do so, a promoter, a unit for regulating transcription and translation, is placed upstream of the 5' end of the DNA of the present invention, and preferably a terminator is placed downstream of the 3' end of the DNA. The promoter and the terminator should be functional in the microorganism to be utilized as a host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75–102(1990)" and "Yeast 8, 423–488 (1992)."

For example, for the genus *Escherichia*, in particular, for *Escherichia coli*, available plasmids include pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc.

For the genus *Bacillus*, available vectors are pUB110 series and pC194 series plasmids; the vectors can be integrated into host chromosome. Available promoters and terminators are derived from apr (alkaline protease), npr (neutral protease), amy (α-amylase), etc.

For the genus *Pseudomonas*, there are host-vector systems developed for *Pseudomonas putida* and *Pseudomonas cepacia*. A broad-host-range vector, pKT240, (containing RSF1010-derived genes required for autonomous replication) based on TOL plasmid, which is involved in decomposition of toluene compounds, is available; a promoter and a terminator derived from the lipase gene (JP-A No. Hei 5-284973) are available.

For the genus *Brevibacterium*, in particular, for *Brevibacterium lactofermentum*, available plasmid vectors include pAJ43 (Gene, 39:281, 1985). Promoters and terminators used for *Escherichia coli* can be utilized without any modification for *Brevibacterium*.

For the genus *Corynebacterium*, in particular, for *Corynebacterium glutamicum*, plasmid vectors such as pCS11 (JP-A Sho 57-183799) and pCB101 (Mol. Gen. Genet., 196:175, 1984) are available.

For the genus *Streptococcus*, plasmid vectors such as pHV1301 (FEMS Microbiol. Lett., 26:239, 1985) and pGK1 (Appl. Environ. Microbiol., 50:94, 1985) can be used.

For the genus *Lactobacillus*, plasmid vectors such as pAMb1 (J. Bacteriol., 137:614, 1979), which was developed for the genus *Streptococcus*, can be utilized; and promoters that are used for *Escherichia coli* are also usable.

For the genus *Rhodococcus*, plasmid vectors isolated from *Rhodococcus rhodochrous* are available (J. Gen. Microbiol., 138:1003, 1992).

For the genus *Streptomyces*, plasmids can be constructed in accordance with the method as described in "Genetic Manipulation of *Streptomyces*: A Laboratory Manual" (Cold Spring Harbor Laboratories (1985)) by Hopwood et al. In particular, for *Streptomyces lividans*, pU486 (Mol. Gen. Genet., 203:468–478, 1986), pKC1064 (Gene, 103:97–99, 1991), and pUWL-KS (Gene, 165:149–150, 1995) are usable. The same plasmids can also be utilized for *Streptomyces virginiae* (Actinomycetol., 11:46–53, 1997).

For the genus *Saccharomyces*, in particular, for *Saccharomyces cerevisiae*, YRp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol., 145:382–390, 1981), plasmids derived from pGK11 and involved in the killer activity, KARS (*Kluyveromyces* autonomous replication sequence) plasmids, and plasmids (refer EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising ARS (autonomous replication sequence) derived from *Schizosaccharomyces pombe* and auxotrophy-complementing selectable markers derived from *Saccharomyces cerevisiae* (Mol. Cell. Biol., 6:80, 1986). Promoters such as ADH promoter derived from *Schizosaccharomyces pombe* are usable (EMBO J., 6:729, 1987). In particular, pAUR224 is commercially available from TaKaRa Shuzo Co., Ltd.

For the genus *Zygosaccharomyces*, plasmids originating from those such as pSB3 (Nucleic Acids Res., 13:4267, 1985) derived from *Zygosaccharomyces rouxii* are available; it is possible to use promoters such as PHO5 promoter derived from *Saccharomyces cerevisiae* and GAP-Zr (Glyceraldehyde-3-phosphate dehydrogenase) promoter (Agri. Biol. Chem., 54:2521, 1990) derived from *Zygosaccharomyces rouxii*.

For the genus *Pichia*, host-vector systems originating from autonomous replication sequences (PARS 1, PARS2) derived from *Pichia* have been developed (Mol. Cell. Biol., 5:3376, 1985), and it is possible to employ a highly efficient promoter such as methanol-inducible AOX promoter, which is available for high-cell-density-culture (Nucleic Acids Res., 15:3859, 1987). Host vector system is developed for *Pichia angusta* (previously called *Hansenula polymorpha*). Although autonomous replication sequences (HARS1 and HARS2) derived from *Pichia angusta* are available as vectors, they are rather unstable. Therefore, multicopy integration to chromosome is effective for them (Yeast, 7:431–443, 1991). In addition, promotors of AOX (alcohol oxidase) and FDH (formate dehydrogenase) induced by methanol and such are available.

For the genus *Candida*, host-vector systems have been developed for *Candida maltosa*, *Candida albicans*, *Candida tropicalis*, *Candida utilis*, etc. An autonomous replication sequence originating from *Candida maltosa* has been cloned (Agri. Biol. Chem., 51:1587, 1987), and a vector using the sequence has been developed for *Candida maltosa*. Further, a chromosome-integration vector with a highly efficient promoter unit has been developed for *Candida utilis* (JP-A Hei 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology, 7:283–287, 1989).

For the genus *Trichoderma*, host-vector systems have been developed for *Trichoderma reesei*, and promoters such as that derived from an extracellular cellulase gene are available (Biotechnology, 7:596–603, 1989).

There are various host-vector systems developed for plants and animals other than microorganisms; in particular, the systems include those of insect such as silkworm (Nature, 315:592–594, 1985), and plants such as rapeseed, maize, potato, etc. These systems are preferably employed to express a large amount of foreign protein.

Microorganisms that possess ability to produce 4-haloacetoacetic acid ester-reducing enzymes used in this invention include all strains, mutants, variants, and transformants that have ability to produce $NAD^+$-dependent (R)-2-octanol dehydrogenase and that belong to the genus *Pichia*, the genus *Candida*, and the genus *Ogataea*, the transformants being constructed by genetic engineering and obtaining ability to produce the enzyme of this invention.

In addition, strains that express the (R)-2-octanol dehydrogenase of this invention obtained by the methods above are available for producing the enzymes of this invention and for producing secondary alcohols and ketones described below.

Thus, the present invention relates to the above-mentioned method for producing secondary alcohols by reducing ketones using (R)-2-octanol dehydrogenase. The (R)-2-octanol dehydrogenase of this invention can use NADH, which is cheaper and more stable than NADPH, as a coenzyme and, therefore, is advantageous for industrial use. The desired oxidation reaction can be carried out by contacting the enzyme of this invention, culture including the enzyme, or processed product thereof with reaction solution.

The forms of contacting the enzyme with reaction solution are not limited to these examples. In the reaction solution, substrate and NADH, which is a coenzyme necessary for the enzymatic reaction, are dissolved in suitable solvent giving environment desired for the expression of the enzymatic activity. Processed products of microorganisms including the (R)-2-octanol dehydrogenase of this invention specifically include microorganisms whose permeability of cell membrane is changed by treatment of organic solvent such as detergent, toluene, and such; cell-free extract obtained by disrupting fungus body with glass beads or by enzyme treatment; partially purified extract thereof; etc.

As ketones in the methods of this invention for producing secondary alcohols, acetophenon, 2-octanone, 4-haloacetoacetic acid ester derivatives, acetonyloxybenzene derivatives represented by the generic formula 1:

Generic Formula 1

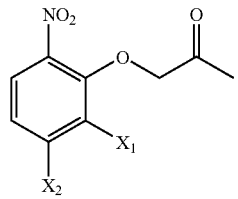

(where each of x1 and x2 indicates a halogen atom), bromomethylcyclopropylketone, 2-acetylbutyrolactone, 5-chrolo-2-pentanone are suitably used. 4-Haloacetoacetic acid ester derivatives in this invention are compounds obtained by replacing position 4 of acetoacetic acid ester with an arbitrary halogen atom. Alcohols constituting the above-mentioned acetoacetic acid ester can be any alcohols. Halogens of 4-haloacetoacetic acid ester derivatives can be bromine, chlorine, and iodine, and, in particular, chlorine is suitably used. Esters can be esters of alcohols that includes straight-chain, branched-chain, and aromatic substitution, such as methyl ester, ethyl ester, propyl ester, isopropyl ester, butyl ester, octyl ester, benzyl ester, and such, and ethyl ester is most preferably used. The 4-haloacetoacetic acid ester derivative includes a derivative including alkyl including straight chain or branched chain at position 2, or halogen such as chlorine, bromine, iodine, etc. Halogens of acetonyloxybenzene derivatives include bromine, chlorine, iodine, and fluorine, and, in particular, fluorine is preferably used. Especially, 2-acetonyloxy-3,4-difluoronitrobenzene is a useful compound that gives 2,3-difluoro-6-nitro-[[(R)-2-hydroxypropyl]oxy]benzene, which is an intermediate in synthesizing an antibacterial drug ofloxacin.

The present invention also relates to a method for producing ketones by oxidizing secondary alcohols with the above-mentioned (R)-2-octanol dehydrogenase. A ketone, which is a reaction product, can be produced by reacting the (R)-2-octanol dehydrogenase of this invention, microorganism producing the enzyme, or processed product thereof with a secondary alcohol. As secondary alcohols that can be substrates in this invention, alkyl alcohols having halogen or aromatic substitution, and so on, such as 2-propanol, 2-butanol, 2-octanol, 1-phenylethanol, and such can be used.

Furthermore, the enzyme of this invention, microorganism producing the enzyme, or processed product thereof can be used for producing optically active alcohols using asymmetric oxidation ability of (R)-2-octanol dehydrogenase with racemic alcohol as a substrate. In other words, optically active alcohol can be produced by preferentially oxidizing either optical isomer with the enzyme of this invention and by obtaining the remaining optically active alcohol. More specifically, the (R)-2-octanol dehydrogenase of this invention is reacted in the presence of $NAD^+$ with racemates in which the (S) form and (R) form of 2-octanol or 1-phenylethanol are mixed. The (R)-2-octanol dehydrogenase of the present invention, which is excellent in stereoselectivity, acts specifically on the (R) form and oxidizes it to produce ketone. However, because it does not act on the (S) form of the alcohol, the proportion of the (S) form becomes larger gradually. If the (S) form accumulating in this way is separated, the (S) form of the alcohols can be finally recovered from racemates. In this way, (S)-2-octanol can be obtained from (RS)-2-ocatanol, and (S)-phenylethanol can be obtained from (RS)-phenylethanol.

The term "optically active alcohol" used herein means an alcohol that includes more optical isomer than other optical isomers, or an alcohol having enantiomeric excess (ee) of preferably 50% or more, more preferably 90% or more, and even more preferably 95% or more. Moreover, "optical isomer" of this invention can be generally called "optically active substance" or "enantiomer".

The above-mentioned method for producing ketones according to this invention can be combined with regenerating system of NADH. NADH is generated from $NAD^+$ concomitantly with the oxidation reaction catalyzed by (R)-2-octanol dehydrogenase. Regeneration of $NAD^+$ from NADH can be effected by using an enzyme (system) contained in microorganisms, which enables regeneration of NAD$^+$ from NADH or by adding to the reaction system a microorganism or an enzyme capable of producing NAD$^+$ from NADH, for example, glutamate dehydrogenase, NADH oxidase, NADH dehydrogenase, and the like. Furthermore, utilizing the substrate specificity of the enzyme of the present invention, the substrate for the reduction reaction, such as 2-octanone, acetophenone, and such, may be added to the reaction system to concurrently effect regeneration of NAD$^+$ from NADH by the action of the enzyme by itself.

In the same manner, the method for producing alcohols can be combined with regenerating system of NAD$^+$. NAD$^+$ is generated from NADH concomitantly with the reduction reaction. NAD$^+$-reducing ability (e.g., glycolysis) of microorganisms can be utilized to regenerate NADH from NAD$^+$. Such ability can be reinforced by adding glucose or ethanol to the reaction system. Alternatively, microorganisms capable of generating NADH from NAD$^+$, or processed products or enzyme thereof may be added to the reaction system. Regeneration of NADH can be carried out using microorganisms containing formate dehydrogenase, glucose dehydrogenase, malate dehydrogenase, glycerol dehydrogenase, alcohol dehydrogenase, or the like, or processed products or purified enzyme thereof. For example, NADH can be regenerated using the conversion of glucose into δ-gluconolactone in the case of the glucose dehydrogenase above. Utilizing the property of the (R)-2-octanol dehydrogenase of the present invention, NADH can also be regenerated using the enzyme per se by adding the substrate for the oxidation reaction such as 2-octanol to the reaction system.

Reactants necessary for NADH regeneration reaction can be added to the reaction system for producing alcohol of the present invention as they are, or as their immobilized products. The reactants can also be contacted with the reaction system through a membrane that enables exchanging NADH.

When the microorganism transformed with a recombinant vector including the DNA of this invention is used alive for producing the above alcohol, an additional reaction system for NADH regeneration can be sometimes omitted. Namely, by using microorganisms that has high activity of NADH regeneration, efficient reduction reaction using transformants can be performed without adding enzymes for NADH regeneration. Moreover, by introducing, into a host, a gene for glucose dehydrogenase, formate dehydrogenase, alcohol dehydrogenase, amino acid dehydrogenase, organic acid dehydrogenase (for example, malate dehydrogenase, and such), and such, which are available for NADH regeneration, simultaneously with a DNA encoding the NAD$^+$-dependent (R)-2-octanol dehydrogenase of the present invention, more efficient expression of the NADH regeneration enzyme and the NAD$^+$-dependent (R)-2-octanol dehydrogenase, and reducton reaction can be performed. For introducing these two or more genes into a host, a method for transforming the host with multiple recombinant vectors obtained by separately introducing, to avoid incompatibility, the genes into multiple vectors whose replication origins are different, a method in which both genes are introduced into a single vector, or a method for introducing both genes into chromosomes is available.

Examples of glucose dehydrogenases that are available for NADH regeneration in this invention include a glucose dehydrogenase derived from *Bacillus subtilis*. In addition, Examples of formate dehydrogenases include a formate dehydrogenase derived from *Mycobacterium vaccae*. The genes encoding these enzymes have been already cloned. Alternatively, such genes can be obtained from the microorganisms by PCR or hybridization screening based on the revealed nucleotide sequences.

When multiple genes are introduced into single vector, each gene can be ligated to the region involved in the regulation of expression, such as promotor or terminater. Multiple genes can also be expressed as operon including multiple cistrons like lactose operon.

The oxidation reaction or reduction reaction using the enzyme of the present invention can be carried out in water, in a water-insoluble organic solvent such as ethyl acetate, butyl acetate, toluene, chloroform, n-hexane, etc., or in the two-phase system of such an organic solvent and aqueous medium such as ethanol, acetone, etc.

The reaction of the present invention can be achieved by using immobilized enzymes, membrane reactors, etc.

Enzymatic reaction by (R)-2-octanol dehydrogenase of this invention can be done under the following conditions:
 reaction temperature: 4 to 60° C., preferably 10 to 37° C.
 pH: 3 to 11, preferably 5 to 10, more preferably 6.0 to 9.0
 concentration of substrate: 0.01 to 90%, preferably 0.1 to 30%

If necessary, 0.001 mM to 100 mM or preferably 0.01 to 10 mM coenzyme NAD$^+$ or NADH can be added to the reaction system. Although the substrate can be added at once at the start of reaction, it is preferable to be added continually or discontinuously so as not to make the concentration of the substrate in the reaction mixture too high.

The compound to be added to the reaction system for regenerating NADH, include, for example, glucose in the case of using glucose dehydrogenase, formic acid in the case of using formate dehydrogenase, ethanol or 2-propanol in the case of the using alcohol dehydrogenase, and can be added at a molar ratio to a substrate ketone of 0.1:20, and preferably in 0.5 to 5 times excess amount to a substrate ketone. The enzymes for regenerating NADH such as glucose dehydrogenase, formate dehydrogenase, or alcohol dehydrogenase can be added in 0.1 to 100 times, and preferably 0.5 to 20 times amount of the enzymatic activity compared with that of the NAD$^+$-dependent (R)-2-octanol dehydrogenase of the invention.

Alcohols produced by reduction of ketones and alcohols produced by asymmetric oxidation of racemic alcohols in this invention can be purified by properly combining centrifugation of microbial cells and proteins, separation by membrane treatment and such, solvent extraction, distillation, etc.

For example, as to 4-halo-3-hydroxybutyric acid esters, after a reaction mixture that includes microbial cells bodies is centrifuged to remove the microbial cells, a solvent such as ethyl acetate, toluene, and such is added to the supernatant to extract 4-halo-3-hydroxybutyric acid esters in the solvent layer. Distilling it after phase separation enables purifying highly pure 4-halo-3-hydroxybutyric acid esters.

The enzyme of this invention used for these various synthetic reactions is not limited to purified enzyme and includes partially purified enzyme, microbial cells including this enzyme, and processed product thereof. The term "processed product" used herein collectively means microbial cells, purified enzyme, partially purified enzyme, or the like that is fixed by various methods. The enzyme constituting the enzymatic reaction of this invention can be used in immobilized forms. The method for immobilization the enzyme is not particularly limited. For example, the methods for immobilizing the enzyme using glutaraldehyde, acrylamide, κ-carrageenan, calcium alginate, ion exchange resin, Celite, and such are known. The reaction of this invention can be conducted using membrane reactor, etc. Membranes that can constitute a membrane reactor are exemplified by ultrafilter, hydrophobic membrane, cationic membrane, nanofiltration membrane (J. Ferment. Bioeng., 83:54–58, 1997) etc.

All references cited herein are incorporated by reference.

DETAILED DESCRIPTION

Figure 1:
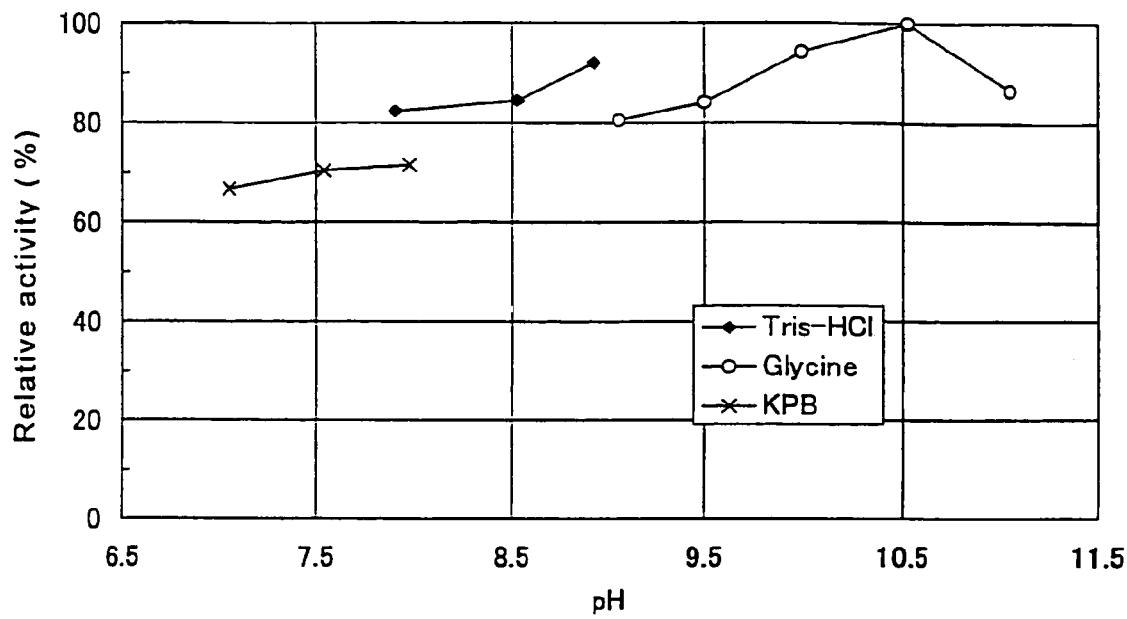
FIG. 1 shows the effect of pH change on enzymatic activity of (R)-2-octanol dehydrogenase purified from *Pichia finlandica*. The longitudinal axis indicates relative activity with taking the maximal activity of the (R)-2-octanol dehydrogenase as 100.

The present invention is illustrated in detail below with references to examples, but is not to be construed as being limited thereto.

EXAMPLE 1

Screening of (R)-2-octanol Dehydrogenase (R)-2-octanol dehydrogenase from yeast was screened by activity staining method using electrophoresis, substrate of (R)- or (S)-2-octanol, and reaction mixture containing $NAD^+$, phenazine methosulfate (PMS), and nitroblue tetrazolium (NBT). Composition of the reaction mixture is as follows:

5 mM of (S)— or (R)-2-octanol
1.3 mM of $NAD^+$
0.13 mM of PMS
0.48 mM of NBT

As a result, the enzymes that were not stained when the substrate was (S)-2-octanol, but were stained preferentially when the substrate was (R)-2-octanol were found in the following yeast strain. These enzymes having (R)-2-octanol dehydrogenase activity also possessed the activity to produce (S)-4-chloro-3-hydroxybutyric acid ethyl ester by reducing 4-chloroacetoacetic acid ethyl ester.
Pichia finlandica: DSM 70280, DSM 1380
Pichia jadinii: DSM 2361, DSM 70167, IFO 0987
Candida utilis: IFO 0988, IFO 0626
Ogataea wickerhamii: IFO 1706

EXAMPLE 2

Cultural Condition for Producing (R)-2-octanol Dehydrogenase

Strains producing (R)-2-octanol dehydrogenase of Example 1 were cultured in 2% glycerol or 1% methanol changed from 2% glucose as carbon source. As a result, Pichia finlandica induced the enzyme in all cultures. Candida utilis strongly induced the enzyme when methanol was used as carbon source.

EXAMPLE 3

Purification of (R)-2-octanol Dehydrogenase From Pichia finlandica

Pichia finlandica DSM 70280 strain was cultured in 4.8 L of medium A and the microbial cells were prepared by centrifugation. Obtained microbial cells were suspended in 100 mM Tris-HCl buffer (pH 8.0), 10% glycerol, 1 mM ethylenediaminetetraacetic acid 2Na (EDTA·2Na), 0.02% 2-mercaptoethanol, and 2 mM phenyl methane sulfonylfluoride (PMSF) and homogenized with bead beater (Biospec). After that, microbialo cell debris were removed by centrifugation and cell-free extract was obtained. Protamine sulphate was added to this cell-free extract, and supernatant was obtained by centrifugation to remove nucleic acid. Ammonium sulfate was added to the supernatant, and the precipitated fraction was obtained in 40% to 75% saturation. Standard buffer including 30% saturated ammonium sulfate was added to the precipitated fraction, the enzyme solution including 40% (final concentration) saturated ammonium sulfate was obtained. Supernatant was obtained by centrifuging the enzyme solution. The supernatant was added to Phenyl-Toyopearl 650M (5.0 cm×25 cm) equilibrated with standard buffer including 30% saturated ammonium sulfate, and gradient elution was conducted with 30% to 0% saturated ammonium sulfate. Composition of medium A and the standard buffer used are followings:
medium A:
  10 g/L yeast extract
  20 g/L peptone
  20 g/L glucose
  pH 6.0
standard buffer:
  10 mM Tris-HCl buffer (pH 8.0)
  0.01% 2-mercaptoethanol
  10% glycerol The activity of (R)-2-octanol dehydrogenase was observed in the part of gradient elution. This peak was recovered and concentrated by ultrafiltration.

After the enzyme solution concentrated was dialyzed with the standard buffer, supernatant was obtained by centrifuging the solution. The supernatant was added to Blue-Sepharose CL-6B (5 cm×10 cm) and washed with the standard buffer, and concentration gradient elution with 0 to 1.5 M sodium chloride was conducted. As the activity of (R)-2-octanol dehydrogenase was eluted in the part of gradient elution, this fraction was recovered and concentrated. After the concentrated enzyme solution was dialyzed with the standard buffer (pH 8.5), added to DEAE-Sepharose FF (1.6 cm×10 cm), and washed with the standard buffer, the concentration gradient elution with 0 to 1 M sodium chloride was conducted. As the activity of (R)-2-octanol dehydrogenase was eluted in the part of fraction passed through and gradient elution, these active fractions were recovered and concentrated. Gel filtration of the enzyme solution obtained from the fraction passed through was conducted using Superdex 200 (0.32 cm×30 cm, SMART system, Amersham Pharmacia Biotech) with standard buffer including 0.3 M sodium chloride. The enzyme was obtained by concentrating the active fraction of gel filtration.

The highest specific activity of the purified enzyme was about 91 U/mg-protein which is the activity of oxidizing (R)-2-octanol. Summary of the purification is shown in Table 1.

TABLE 1

| Step | Amount of protein (mg) | Total activity (U) | Specific activity (U/mg) |
| --- | --- | --- | --- |
| Cell-free extract | 26,900 | 603 | 0.0224 |
| Nucleic acid removal | 10,900 | 588 | 0.0540 |
| Ammonium sulfate 40–75% | 5,560 | 361 | 0.0649 |
| Phenyl-Toyopearl | 398 | 162 | 0.408 |
| Blue-Sepharose | 11.7 | 46.9 | 3.59 |
| DEAE-Sepharose | 0.880 | 4.53 | 5.15 |
| Superdex 200 | 0.00288 | 0.262 | 91.1 |

EXAMPLE 4

Measuring Molecular Weight of (R)-2-octanol Dehydrogenase

As a result of SDS-PAGE, it was revealed that molecular weight of the enzyme of Example 3 from Pichia finlandica was about 30,000 Da. When using gel filtration column of Superdex 200, the molecular weight was about 83,000 Da.

EXAMPLE 5

Optimum pH of (R)-2-octanol Dehydrogenase

We examined (R)-2-octanol dehydrogenase activity of the enzyme obtained from Example 3 changing pH by using phosphate buffer (KPB), Tris-HCl buffer, Glycine buffer. FIG. 1 shows relative activity with taking the maximal activity as 100. As a result, the optimum pH of the enzyme was from 8.0 to 11.0.

Figure 2:
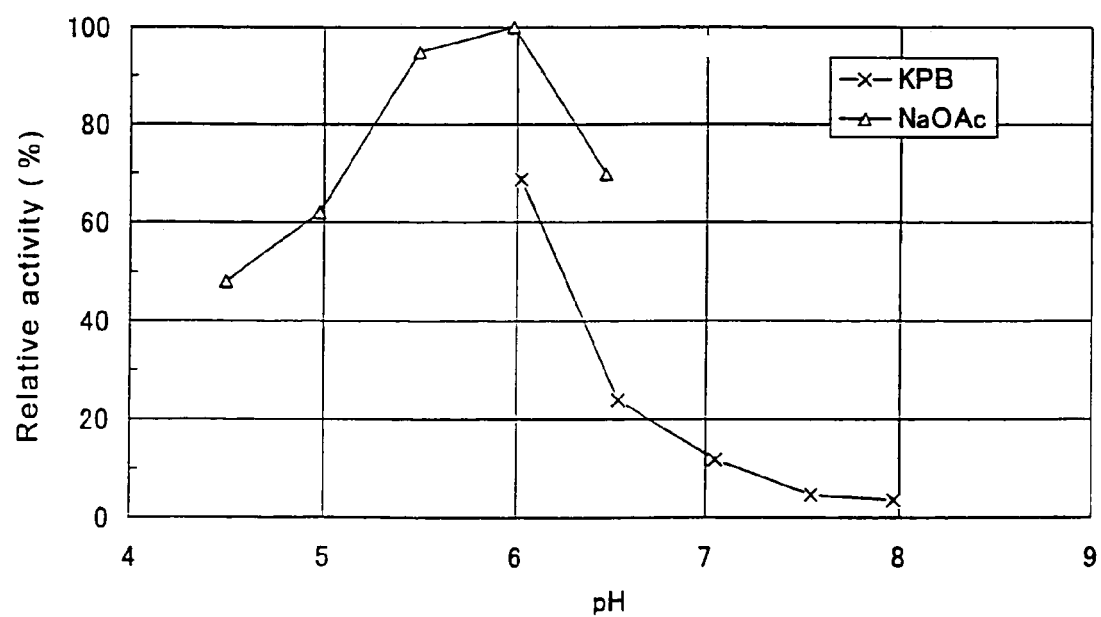
FIG. 2 shows the effect of pH change on the ethyl 4-chloroacetoacetate-reducing activity of (R)-2-octanol dehydrogenase purified from *Pichia finlandica*. The longitudinal axis indicates relative activity with taking the maximal activity as 100.

Then, we examined 4-chloroacetoacetic acid ethyl ester reductase activity of the enzyme obtained from Example 3 changing pH by using phosphate buffer (KPB), Tris-HCl buffer, and Glycine buffer. FIG. 2 shows relative activity with taking the maximal activity as 100. As a result, the optimum pH of the enzyme was from 5.0 to 6.5.

EXAMPLE 6

Optimum Temperature of (R)-2-octanol Dehydrogenase

Figure 3:
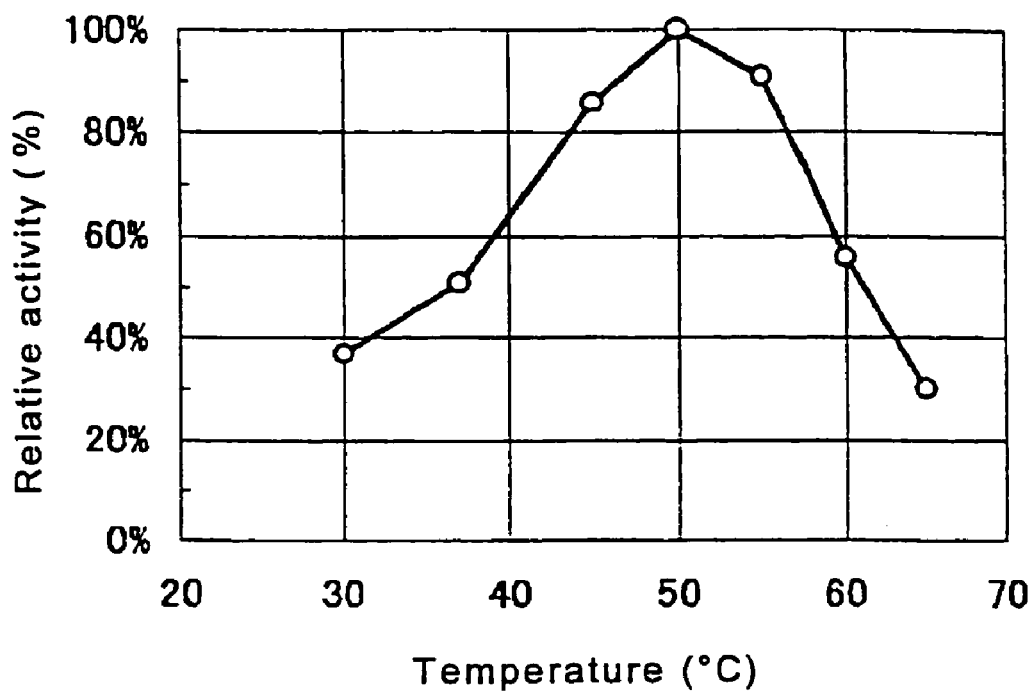
FIG. 3 shows the effect of temperature change on the oxidation activity of (R)-2-octanol dehydrogenase purified from *Pichia finlandica*. The longitudinal axis indicates relative activity with taking the maximal activity as 100.

We examined (R)-2-octanol oxidation activity of the enzyme obtained from Example 3 changing only temperature in the standard reaction conditions. FIG. 3 shows relative activity with taking the maximal activity as 100. As a result, the optimum temperature of the enzyme was from 45 to 55.

Figure 4:
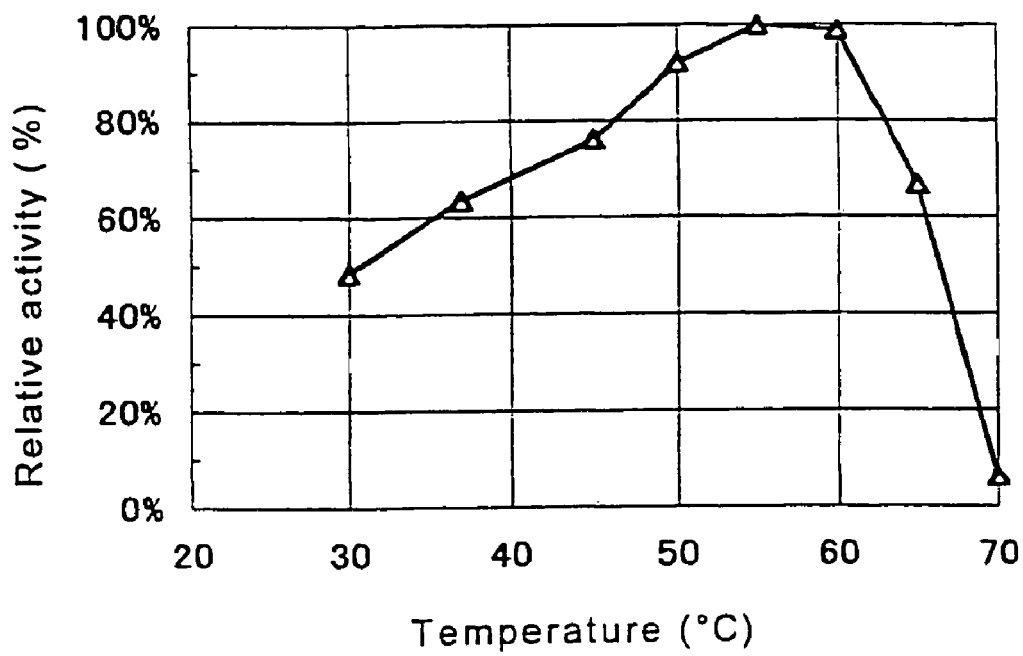
FIG. 4 shows the effect of temperature change on the ethyl 4-chloroacetoacetate-reducing activity of (R)-2-octanol dehydrogenase purified from *Pichia finlandica*. The longitudinal axis indicates relative activity with taking the maximal activity as 100.

We examined 4-chloroacetoacetic acid ethyl ester reductase activity of the enzyme obtained from Example 3 changing only temperature in the standard reaction conditions. FIG. 4 shows relative activity with taking the maximal activity as 100. As a result, the optimum temperature of the enzyme was from 55 to 60.

EXAMPLE 7 pH Range for Enzyme Stability

Figure 5:
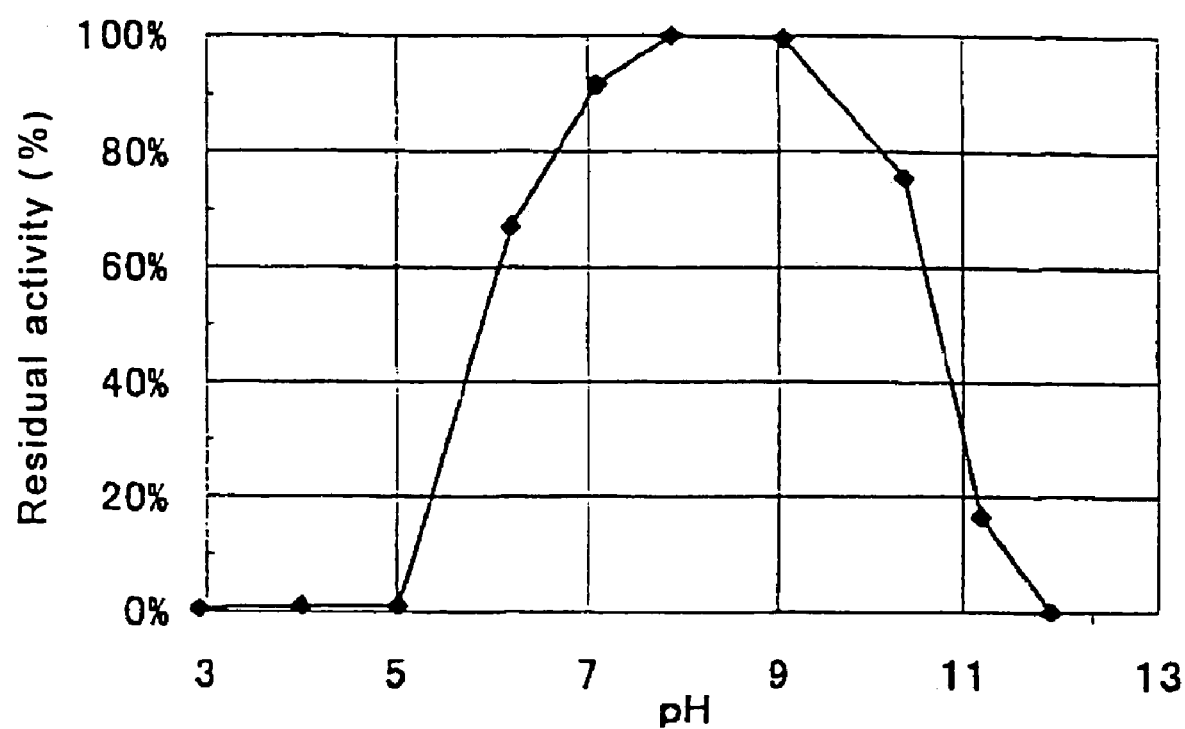
FIG. 5 shows the residual activity of (R)-2-octanol dehydrogenase purified from *Pichia finlandica*. The longitudinal axis indicates residual activity with taking the activity of untreated enzyme as 100.

The enzyme of Example 3 was incubated at 30° C. for 30 minutes in Britten-Robinson buffer pH 3 to 12, and the residual activity was measured. FIG. 5 shows residual activity with taking the activity of the untreated enzyme as 100. The enzyme was stablest at the pH ranging from 8.0 to 9.0.

EXAMPLE 8

Substrate Specificity of (R)-2-octanol Dehydrogenase

The (R)-2-octanol dehydrogenase was reacted with various alcohols and its oxidation activity was measured. Table 2 shows relative activities with taking the oxidation activity of the (R)-2-octanol as 100 using $NAD^+$ as a coenzyme.

TABLE 2

| Substrate (oxidization reaction) | |
|---|---|
| (R)-2-octanol | 100 |
| (S)-2-octanol | 4.73 |
| 2-Propanol | 6.79 |
| 1-Octanol | 1.72 |
| Ethyl (R)-4-chloro-3-hydroxybutyrate | 0.172 |
| Ethyl (S)-4-chloro-3-hydroxybutyrate | 2.24 |
| (R)-1-phenylethanol | 255 |
| (S)-1-phenylethanol | 1.81 |
| Ethyl (R)-3-hydroxybutyrate | 41.1 |
| Ethyl (S)-3-hydroxybutyrate | 1.03 |
| Ethanol | 0.688 |
| (R)-2-butanol | 49.3 |
| (S)-2-butanol | 7.31 |
| Cyclohexanol | 0.172 |
| (R)-1-phenyl-1,3-propanediol | 0.344 |
| (S)-1-phenyl-1,3-propanediol | 0.258 |
| 2-Hexanol | 54.1 |
| (R)-1,3-butanediol | 1.29 |
| (S)-1,3-butanediol | 0.516 |
| 2-Octanol | 77.8 |
| 1-Phenoxy-2-propanol | 15.5 |

As a result, the relative activity was 4.7% for (S)-2-octanol, 6.8% for 2-propanol, and 255% for (R)-1-phenylethanol.

The enzyme of Example 3 was reacted with various ketones and its reduction activity was measured. Table 3 shows relative activities with taking the reduction activity of the 4-chloroacetoacetic acid ethyl ester as 100 using NADH as a coenzyme.

TABLE 3

| Substrate (reduction reaction) | |
|---|---|
| Ethyl 4-chloroacetoacetate | 100 |
| 2-Octanone | 31.2 |
| Acetophenone | 45.3 |
| Ethyl acetoacetate | 106 |
| 1-Phenoxy-2-propanone | 54.2 |
| Propionaldehyde | 18.4 |
| 4-Hydroxy-2-butanone | 0.691 |
| Acetone | 1.82 |
| 2-Butanone | 7.99 |

As a result, the relative activity was 31.2% for 2-octanone and 45% for acetophenone.

EXAMPLE 9

Behavior of (R)-2-octanol Dehydrogenase to Reagents

The (R)-2-octanol dehydrogenase was treated with various reagents at 30° C. for 30 minutes and the (R)-2-octanol dehydrogenase activity was measured. Table 4 shows the resulting residual activities with taking the activity of the enzyme that was treated without reagents at 30° C. for 30 minutes as 100. The (R)-2-octanol dehydrogenase of this invention was slightly inhibited by mercury chloride and ethylenediaminetetraacetic acid 2Na (EDTA·2Na). The enzyme was stabilized with N-ethylmaleimide, o-phenanthroline, magnesium chloride, calcium chloride, and manganese chloride.

TABLE 4

| Reagent | Concentration (mM) | Residual activity (%) |
|---|---|---|
| Control | — | 100 |
| Phenylmethylsulfonyl fluoride | 1 | 111 |
| Mercury p-chlorobenzoate | 0.05 | 118 |
| N-ethylmaleimide | 1 | 147 |
| EDTA·2Na | 1 | 81 |
| o-Phenanthroline | 1 | 162 |
| Dithiothreitol | 1 | 123 |
| $NH_2OH \cdot HCl$ | 0.01 | 99 |
| Quercetin | 0.1 | 99 |
| KCl | 1 | 106 |
| $MgCl_2 \cdot 6H_2O$ | 1 | 185 |
| $CaCl_2 \cdot 2H_2O$ | 1 | 174 |
| $MnCl_2 \cdot 4H_2O$ | 1 | 185 |
| $FeCl_2$ | 1 | 93 |
| $CoCl_2 \cdot 6H_2O$ | 1 | 99 |
| $NiCl_2 \cdot 6H_2O$ | 1 | 103 |
| $ZnCl_2$ | 1 | 96 |
| $BaCl_2 \cdot 2H_2O$ | 1 | 102 |
| $CuSO_4$ | 1 | 100 |
| $HgCl_2$ | 0.01 | 62 |

EXAMPLE 10

Activation of (R)-2-octanol Dehydrogenase by Reagents

The activation effect of (R)-2-octanol dehydrogenase in various reagents was measured. Table 5 shows the resulting activities with taking the activity without reagents as 100. The (R)-2-octanol dehydrogenase of this invention was activated by magnesium, manganese, and zinc ions. For anions, sulphate ion activated the enzymatic activity.

TABLE 5

| Reagent | Concentration (mM) | Relative activity (%) |
|---|---|---|
| Control | — | 100 |
| MgCl$_2$N6H$_2$O | 1 | 122 |
| MgSO$_4$ | 1 | 125 |
| MnCl$_2$N4H$_2$O | 1 | 114 |
| MnSO$_4$N4-5H$_2$O | 1 | 121 |
| ZnCl$_2$ | 1 | 105 |
| ZnSO$_4$N7H$_2$O | 1 | 110 |

EXAMPLE 11

Partial Amino Acid Sequences of (R)-2-octanol Dehydrogenase

N terminal amino acid sequence was analyzed by protein sequencer using the enzyme of Example 3, but the N terminal amino acid was blocked. Then, purified enzyme was isolated by SDS-PAGE, and the gel including (R)-2-octanol dehydrogenase was cutted out. Tris buffer including trypsin was added to the gel and it was treated at 35° C. for 20 hours. After that, the sample solution was treated with reverse-phase HPLC, and peptide fragments were isolated. The peptide fragments were analyzed by protein sequencer. As a result, 3 kinds of amino acid sequences were obtained. Amino acid sequences of peptide A, B, and C are shown in SEQ ID NO:3, 4, and 5 respectively.

```
SEQ ID NO: 3: peptide A
Val-Ala-Val-Val-Thr-Gly-Ala-Leu-Ser-Gly

SEQ ID NO: 4: peptide B
Leu-Ile-Ser-Glu-Thr-Leu-Ala-Thr-Phe-Gly-Gly-Leu

SEQ ID NO: 5: peptide C
Leu-Gly-Arg-Pro-Glu-Glu-Val-Ala-Asp-Ala
```

EXAMPLE 12

Preparation of Chromosome DNA from *Pichia finlandica*

The chromosome DNA was purified from *Pichia finlandica* by the method of Cryer (Meth. Cell Biol., 12:39–44, 1975).

EXAMPLE 13

PCR Cloning of Core Region of (R)-2-octanol Dehydrogenase Gene

The sense primer corresponding to peptide A and the antisense primer corresponding to peptide C were synthesized. BamHI restriction enzyme site (GTCGGATCC) was added to the 5' terminal of each primer. The nucleotide sequence of each primer is shown in SEQ ID NO:6 (primer A) and SEQ ID NO:7 (primer C).

```
SEQ ID NO: 6: primer A
GTCGGATCCGTBGCHGTBGTBACHGGHGC

SEQ ID NO: 7: primer C
GTCGGATCCGCRTCNGCNACYTCYTCNGG
```

PCR was conducted with 50 µL reaction solution including 50 pmol each primer A and C, 10 nmol dNTP, 100 ng chromosome DNA from *Pichia finlandica*, buffer for ExTaq (Takara), and ExTaq 2U (Takara). PCR condition was 30 cycles of denature at 94° C. for 30 seconds, annealing at 37° C. for 30 seconds, and extension at 70° C. for 1 minute. As a result, the specific PCR product was amplified.

EXAMPLE 14

Subcloning of PCR Fragment of Core Region of (R)-2-octanol Dehydrogenase Gene

Each DNA fragment amplified in the PCR was extracted with phenol/chloroform, recovered by ethanol precipitation, and digested with BamHI restriction enzyme. After 2% agarose gel electrophoresis, bands having appropriate length were cutted out, with Sephaglas (Pharmacia), and recovered. Each DNA fragment obtained was ligated to pUC 18 (Takara) digested with BamHI restriction enzyme with Takara Ligation Kit Ver.2. Then, *Escherichia coli* (*E. coli*) strain JM109 strain was transformed with it. Transformed strain was incubated on the plate including LB medium (1% bacto-trypton, 0.5% bact-yeast extract, and 1% sodium chloride) with 50 µg/mL ampicillin, 50 µg/mL 5-bromo-4-chloro-3-indolyl-β-D-galactopyranoside, and 20 µg/mL isopropylthio-β-D-galactopyranoside (IPTG). Some white colonies were cultured in liquid LB medium including ampicillin, and plasmids including the DNA fragments were purified with Flex-Prep (Pharmacia).

Using the plasmid, nucleotide sequence of the inserted DNA was analyzed. PCR was conducted with BigDye Terminator Cycle Sequencing FS Ready Reaction Kit (Applied Biosystems), and the DNA nucleotide sequence was analyzed with PRISM 310 Genetic Analyzer Kit (Applied Biosystems). The nucleotide sequence of the core region determined is shown in SEQ ID NO:8: PF—CORE.

EXAMPLE 15

Subcloning of DNA Around the Core Region of (R)-2-octanol Dehydrogenase Gene

Chromosome DNA from *Pichia finlandica* was digested with BstYI, NspI, and PstI restriction enzymes. Each fragment was cyclized by self-ligation with T4 ligase at 16° C. overnight. BamHI restriction enzyme site (GTCGGATCC) was added to the 5' terminal of primers PfOD-c5u (SEQ ID NO:9) and PfOD-c3d (SEQ ID NO:10). PCR was conducted with 50 µL reaction solution including 50 pmol each above primer, 10 mmol dNTP, 125 ng self-ligated DNA, buffer for ExTaq (Takara), and ExTaq 1U (Takara). PCR condition was 35 cycles of denature at 94° C. for 30 seconds, annealing at 55° C. for 30 seconds, and extension at 70° C. for 7 minute using GeneAmp PCR System 2400 (PerkinElmer). As a result of agarose gel electrophoresis of a fraction of PCR product, DNA fragments of about 3500 bp, 2000 bp, and 4000 bp which corresponded to DNA fragments of the template DNA digested with BstYI, NspI, and PstI respectively were detected.

```
SEQ ID: 9: PfOD-c5u
GTCGGATCCTCAGAGATCGTTACTTTGGC

SEQ ID: 10: PfOD-c3d
GTCGGATCCCGACTCCTTTGATAGATGAG
```

Each DNA fragment amplified in the PCR was extracted with phenol/chloroform, recovered by ethanol precipitation, and digested with BamHI restriction enzyme. After agarose gel electrophoresis, bands having appropriate length were cutted out, with Sephaglas (Pharmacia), and recovered.

Each DNA fragment obtained was ligated to pUC 18 (Takara) digested with BamHI restriction enzyme with Takara Ligation Kit Ver.2. Then, *E. coli* strain JM109 strain was transformed with it. Transformed strain was incubated on the plate including LB medium (1% bacto-trypton, 0.5% bact-yeast extract, and 1% sodium chloride) with 50 µg/mL ampicillin, 50 µg/mL 5-bromo-4-chloro-3-indolyl-p-D-galactopyranoside, and 20 µg/mL isopropylthio-β-D-galactopyranoside (IPTG). Some white colonies were cultured in liquid LB medium including ampicillin, and plasmids including the DNA fragments were purified with Flex-Prep (Pharmacia). The plasmids obtained were pPF-Bst, pPF-Nsp, and pPF-Pst which correspond to the restriction enzymes used for the preparation BstYI, NspI, and PstI respectively.

The nucleotide sequence of the inserted DNA was analyzed from the purified plasmids. PCR was conducted with BigDye Terminator Cycle Sequencing FS Ready Reaction Kit (Applied Biosystems), and the DNA nucleotide sequence was analyzed with PRISM 310 Genetic Analyzer Kit (Applied Biosystems). The analyzed nucleotide sequences of the inserted DNA of pPF-BST, pPF-Nsp, and pPF-Pst were separated to 5'-upstream region and 3'-downstream region of the core region and shown as PF-5U (SEQ ID NO:11) and PF-3D (SEQ ID:12).

The nucleotide sequence of PF-5U, PF-3D, and PF-CORE were synthesized, and the sequence of (R)-2-octanol dehydrogenase was determined by open reading frame (ORF) search. The nucleotide sequence determined is shown in SEQ ID NO:1, and the amino acid sequence encoding the nucleotide sequence is shown in SEQ ID NO:2. These synthesis and ORF search was conducted on the software Genetyx-ATSQ/WIN and Genetyx-WIN (Software Developing Company).

EXAMPLE 16

Cloning of (R)-2-octanol Dehydrogenase—1

The primers, PFO-ATG1 (SEQ ID NO:13) and PFO-TAA1 (SEQ ID NO:14) used for construction of expression vector, were synthesized based on the nucleotide sequence of (R)-2-octanol dehydrogenase structural gene. PCR was conducted with 50 µL reaction solution including 10 pmol above each primer, 10 nmol dNTP, 50 ng chromosome DNA from *Pichia finlandica*, buffer for Pfu-DNA polymerase (STRATAGENE), and Pfu-DNA polymerase 1.25 U (STRATAGENE). PCR condition was 30 cycles of denature at 95° C. for 30 seconds, annealing at 50° C. for 1 minute, and extension at 70° C. for 1.5 minutes using GeneAmp PCR System 2400 (PerkinElmer).

```
SEQ ID NO: 13 PFO-ATG1
TCGACATGTCTTATAATTTCCATAACAAG

SEQ ID NO: 14 PFO-TAA1
GCAGAATTCCTCTAGATTACTGGGCTGTGTACCC
```

As a result of agarose gel electrophoresis of a fraction of PCR product, the specific band was detected.

The DNA fragment obtained was extracted with phenol/chloroform and recovered by ethanol precipitation. The DNA fragment was digested with AflIII and EcoRI restriction enzyme. After agarose gel electrophoresis, bands having appropriate length were cutted out, with Sephaglas (Pharmacia).

The DNA fragment obtained was ligated to the plasmid that was pSE420D (Invitrogen) with modified multicloning site (JP-A 2000-189170) digested with NcoI and EcoRI restriction enzyme with Takara Ligation Kit. Then, *E. coli* strain JM109 strain was transformed with it.

Figure 6:
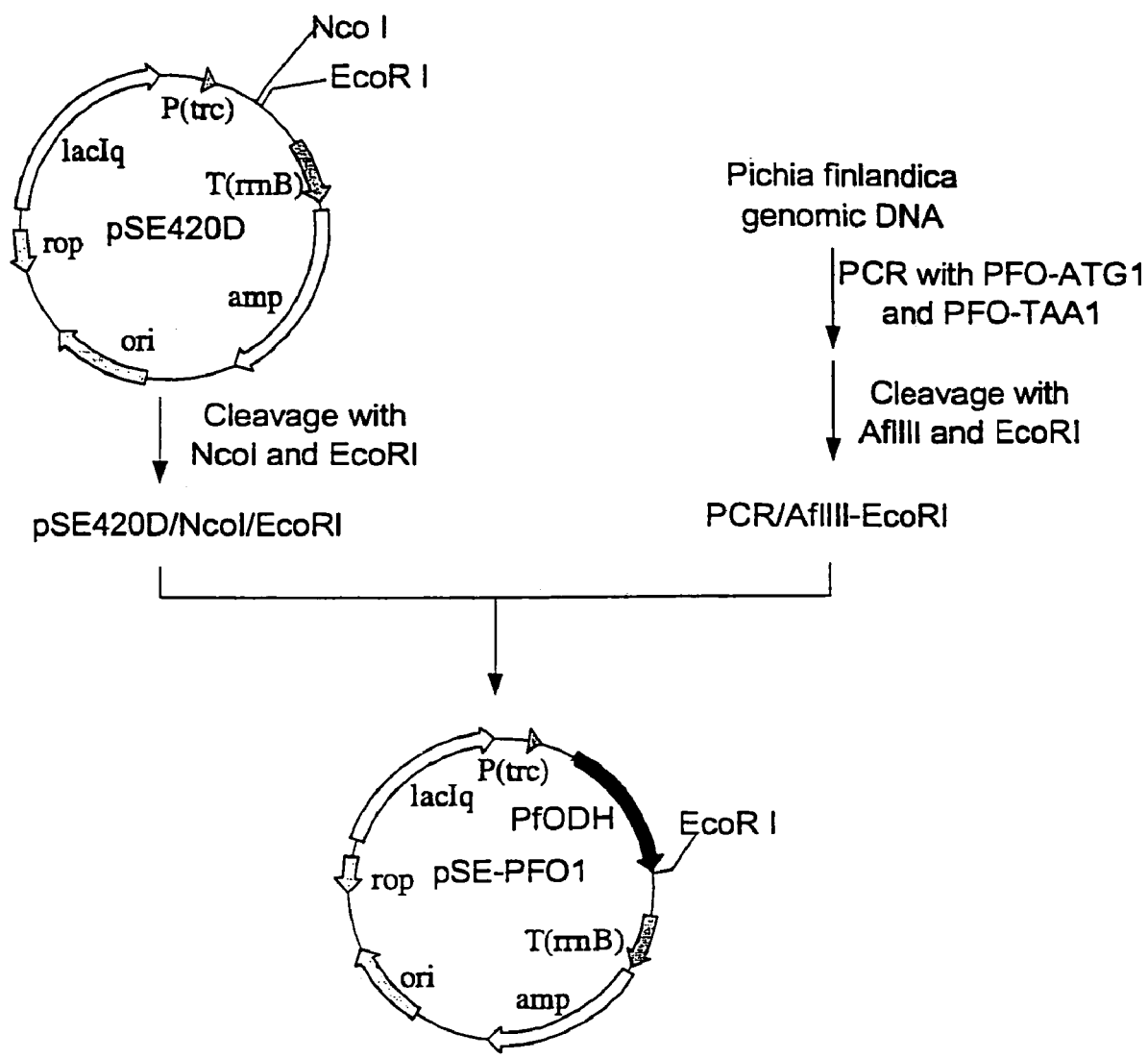
FIG. 6 shows the construction of a plasmid (pSE-PFO1) into which an (R)-2-octanol dehydrogenase gene derived from *Pichia finlandica* is introduced. In the plasmid map, abbreviations are as follows: P(trc), trc promotor: T(rrnB), rrnBT1T2 terminator; Amp, β-lactamase gene showing ampicillin resistance; ori, replication origin of the plasmid; rop, ROP-protein gene; laqIq, lactose repressor. PfODH in pSE-PFO1 indicates the (R)-2-octanol dehydrogenase derived from *Pichia finlandica*.

Transformed strain was incubated with the LB medium plate including 50 µg/mL ampicillin. Plasmids were purified from some colonies, and nucleotide sequence of the inserted fragment was analyzed. The plasmid having (R)-2-octanol dehydrogenase of this invention was named pSE-PF01. FIG. 6 shows the process of constructing the plasmid.

EXAMPLE 17

Cloning of (R)-2-octanol Dehydrogenase—2

The primers, PFO-ATG2 (SEQ ID NO:15) and PFO-TAA2 (SEQ ID NO:16) used for construction of expression vector, were synthesized based on the nucleotide sequence of (R)-2-octanol dehydrogenase structural gene. PCR was conducted with 50 µL reaction solution including 10 pmol above each primer, 10 nmol dNTP, 50 ng chromosome DNA from *Pichia finlandica*, buffer for Pfu-DNA polymerase (STRATAGENE), and Pfu-DNA polymerase 1.25 U (STRATAGENE). PCR condition was 30 cycles of denature at 95° C. for 30 seconds, annealing at 50° C. for 1 minute, and extension at 70° C. for 1.5 minutes using GeneAmp PCR System 2400 (PerkinElmer).

```
SEQ ID NO: 15 PFO-ATG2
CACGAATTCTAAAATGTCTTATAATTTCCATAACAAG

SEQ ID NO: 16 PFO-TAA2
AGTACTAGTATTACTGGGCTGTGTACCC
```

As a result of agarose gel electrophoresis of a fraction of PCR product, the specific band was detected.

The DNA fragment obtained was extracted with phenol/chloroform and recovered by ethanol precipitation. The DNA fragment was digested with EcoRI and SpeI restriction enzyme. After agarose gel electrophoresis, bands having appropriate length were cutted out, with Sephaglas (Pharmacia).

The DNA fragment obtained was ligated to pSE420D digested with EcoRI and SpeI restriction enzyme with Takara Ligation Kit. Then, *E. coli* strain JM109 strain was transformed with it.

Figure 7:
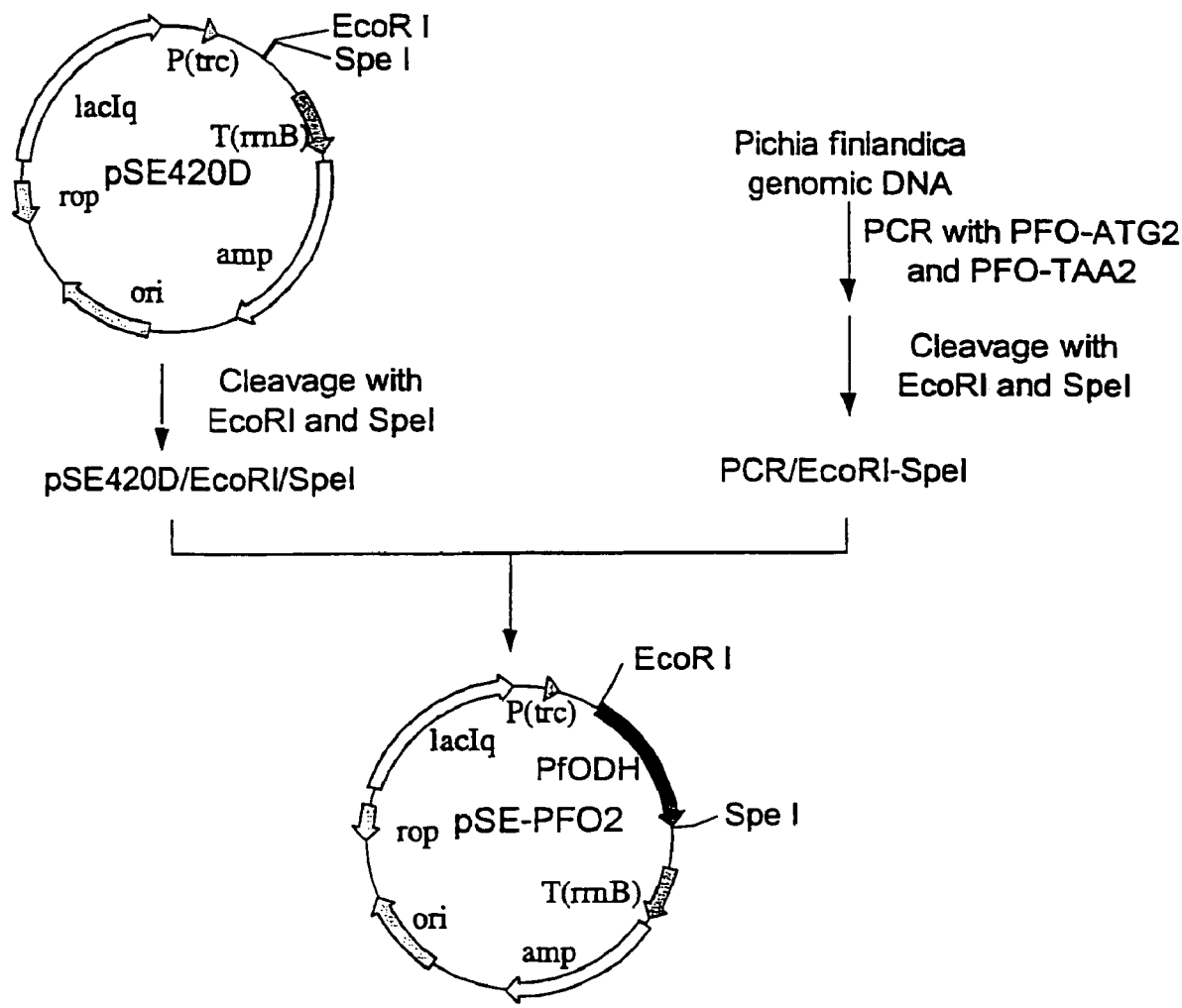
FIG. 7 shows the construction of a plasmid (pSE-PFO2) into which an (R)-2-octanol dehydrogenase gene derived from *Pichia finlandica* is introduced. In the plasmid map, abbreviations are as follows: P(trc), trc promotor; T(rrnB), rrnBT1T2 terminator; Amp, β-lactamase gene showing ampicillin resistance; ori, replication origin of the plasmid; rop, ROP-protein gene; laqIq, lactose repressor. PfODH in pSE-PFO2 indicates the (R)-2-octanol dehydrogenase derived from *Pichia finlandica*.

Transformed strain was incubated with the LB medium plate including 50 µg/mL ampicillin. Plasmids were purified from some colonies, and nucleotide sequence of the inserted fragment was analyzed. The plasmid having (R)-2-octanol dehydrogenase of this invention was named pSE-PF02. FIG. 7 shows the process of constructing the plasmid.

EXAMPLE 18

Production of Recombinant (R)-2-octanol Dehydrogenase by *E. coli*

Strain JM109 transformed with the expression plasmids of (R)-2-octanol dehydrogenase genes, pSE-PF01 and pSE-PF02, were cultured in liquid LB medium including ampicillin overnight at 30° C., added to 0.1 mM IPTG, and cultured for more 4 hours.

After microbial cells were collected by centrifugation, bodies were suspended with 100 mM Tris-HCl buffer (pH 8.5) including 0.02% 2-mercaptoethanol and 1 mM magnesium sulfate and were disrupted by the treatment for 4 minutes with airtight ultrasonic disrupter UCD-200TM (CosmoBio). The supernatant was recovered as extract.

EXAMPLE 19

Activity of Recombinant (R)-2-octanol Dehydrogenase

Activity of the recombinant (R)-2-octanol dehydrogenase of Example 18 to (R)-2-octanol was measured and compared to that of cell-free extract without plasmids. The result is shown in Table 6.

TABLE 6

| Plasmid ü @ | (R)-2-octanol dehydrogenase activity U/mg-protein |
|---|---|
| None | 0.00 |
| pSE-PF01 | 4.16 |
| pSE-PF02 | 1.95 |

EXAMPLE 20

Production of Recombinant (R)-2-octanol Dehydrogenase by Various E. coli Strains Strains HB101, TG1 (*E. coli* DSM 6056), and MG1665 (*E. coli* ATCC 47076) were transformed with the plasmid pSE-PF01 expressing (R)-2-octanol dehydrogenase genes.

Each recombinant *E. coli* were cultured in liquid LB medium overnight at 30° C., added to 0.1 mM IPTG, and cultured for more 4 hours. Two kinds of *E. coli* obtained were collected and their enzymatic activities were measured.

EXAMPLE 21

Activity of Various E. coli Strains Transformed with pSE-PF01

The transformed *E. coli* of Example 20 (corresponding to 2 mL culture medium) was disrupted by the method of Example 18. The extract was prepared for the measurement of enzymatic activity. The activity is shown in Table 7.

TABLE 7

| Host ü @ | (R)-2-octanol dehydrogenase activity U/mg-protein |
|---|---|
| JM109 | 4.16 |
| HB101 | 8.00 |
| TG1 | 11.0 |
| MG1655 | 10.4 |

EXAMPLE 22

Purification of DNA from Bacillus subtilis

*Bacillus subtilis* BGSC 1A1 strain was cultured in LB medium. Chromosome DNA from the strain was using Qiagen Genomic Tip(Qiagen) following the method described in attached manual.

EXAMPLE 23

Cloning of Glucose Dehydrogenase Gene From Bacillus subtilis

To regenerate the reduced form of nicotinamide adenine dinucleotide phosphate, glucose dehydrogenase gene from *Bacillus subtilis* described in the reference (JP-A 2000-189170) was cloned. pSE-BSG1 was obtained following the method described in the reference. The primers, BSG-ATG3 (SEQ ID NO:19) and BSG-TAA3 (SEQ ID NO:20) were synthesized to construct new plasmids based on the 5' terminal and 3' terminal sequence of the structural gene. PCR was conducted using pSE-BSG1 as a template for 30 cycles of 95° C. for 30 seconds, 50° C. for 1 minute, and 75° C. for 3 minutes and Then, the specific band was obtained.

SEQ ID NO: 17: BSG-ATG3
AGACCATGGATCCAATGTATCCAGATTTAAAAGGAA

SEQ ID NO: 18: BSG-TAA3
GAATCTAGATTAACCGCGGCCTGCCTG

Figure 8:
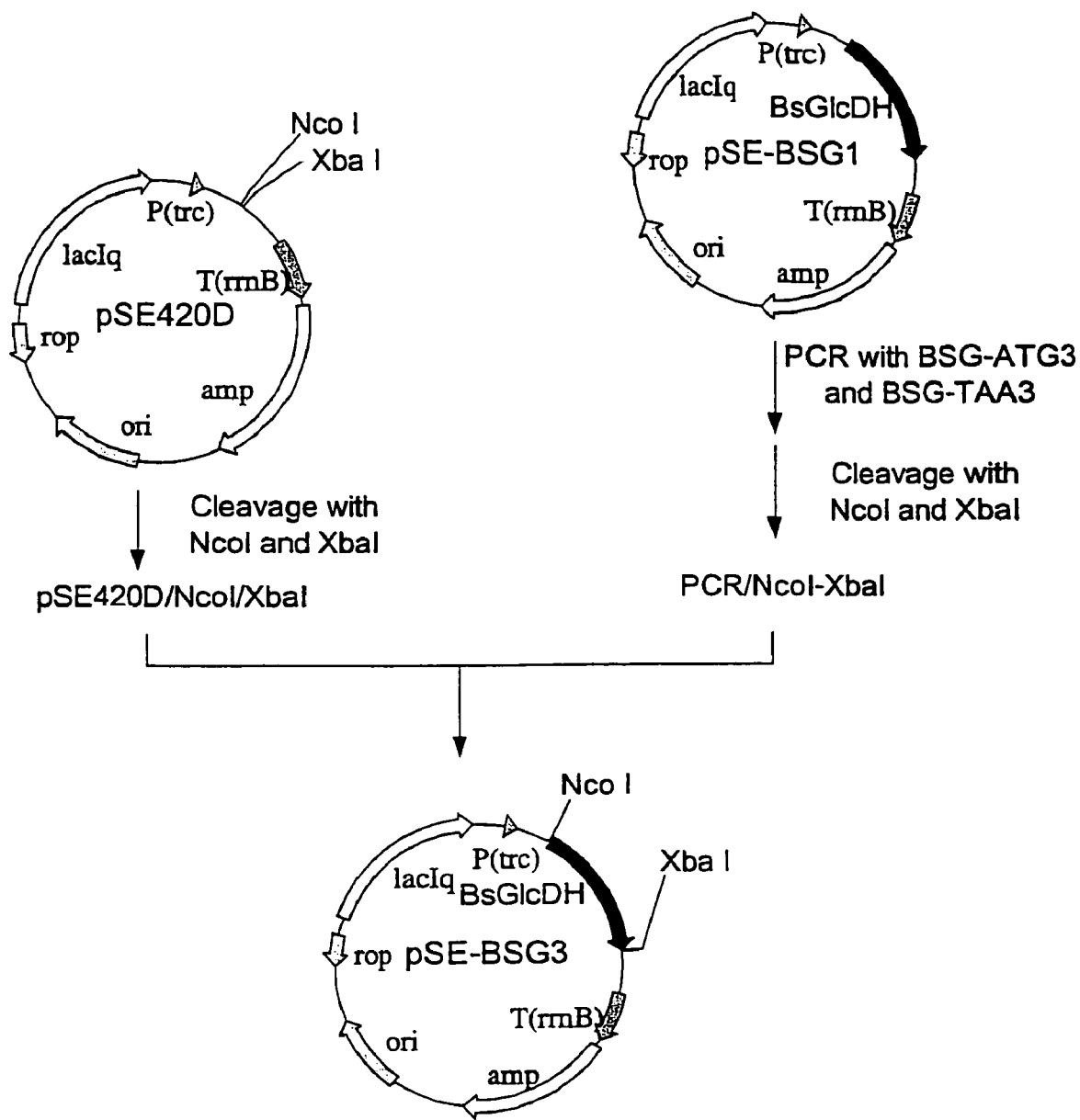
FIG. 8 shows the construction of the plasmid (pSE-BSG3) into which a glucose dehydrogenase gene derived from *Bacillus subtilis* is introduced. In the plasmid map, abbreviations are as follows: P(trc), trc promotor: T(rrnB), rrnBT1T2 terminator; Amp, β-lactamase gene showing ampicillin resistance; ori, replication origin of the plasmid; rop, ROP-protein gene; laqIq, lactose repressor; BsGlcDH, glucose dehydrogenase gene derived from *Bacillus subtilis*.

The obtained DNA fragment was digested with NcoI and XbaI restriction enzyme. The plasmid vector was also digested with NcoI and XbaI. The DNA fragment amplified by PCR digested both enzyme were ligated to the plasmid with T4 DNA ligase and pSE-BSG3 was obtained. FIG. 8 shows the process of constructing the plasmid.

EXAMPLE 24

Construction of Plasmid pSG-PF01 Co-Expressesing (R)-2-octanol Dehydrogenase Gene Derived from Pichia finlandica and Glucose Dehydrogenase Gene Derived from Bacillus subtilis A DNA fragment that includes an (R)-2-octanol dehydrogenase gene derived from *Pichia finlandica* was prepared by digesting pSE-PF01 constructed in Example 15 with two restriction enzymes, MluI and EcoRI.

Figure 9:
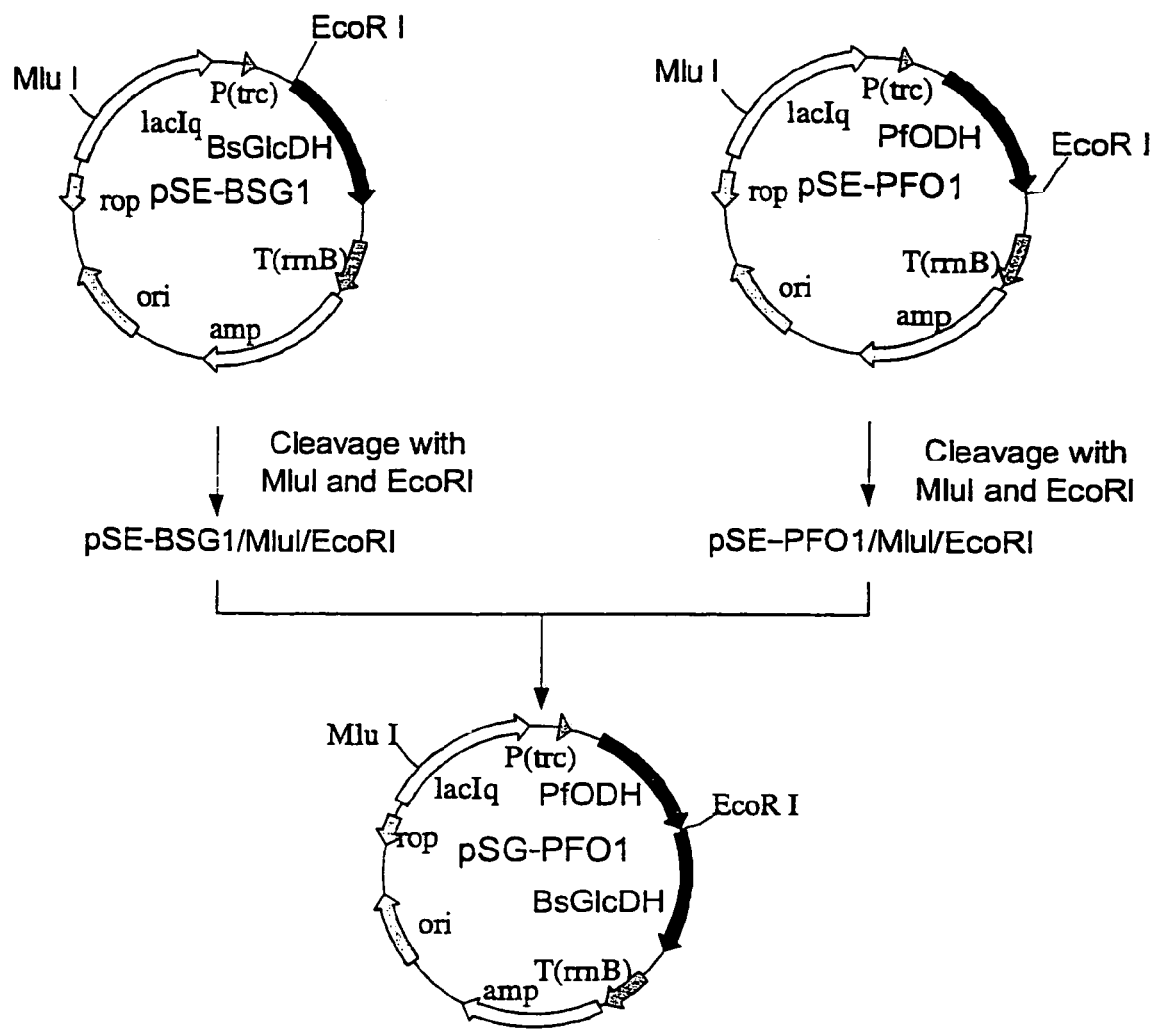
FIG. 9 shows the construction of the plasmid (pSG-PFO1) into which an (R)-2-octanol dehydrogenase gene derived from *Pichia finlandica* and a glucose dehydrogenase gene derived from *Bacillus subtilis* are introduced. In the plasmid map, abbreviations are as follows: P(trc), trc promotor: T(rrnB), rrnBT1T2 terminator; Amp, β-lactamase gene showing ampicillin resistance; ori, replication origin of the plasmid; rop, ROP-protein gene; laqIq, lactose repressor; BsGlcDH, glucose dehydrogenase gene derived from *Bacillus subtilis*; PfODH, (R)-2-octanol dehydrogenase gene derived from *Pichia finlandica*.

The plasmid pSE-BSG1, which was constructed in Example 23 and includes a glucose dehydrogenase gene derived from *Bacillus subtilis*, was digested with two restriction enzymes, MluI and EcoRI, to prepare a DNA fragment including the glucose dehydrogenase gene derived from *Bacillus subtilis*. The fragment was ligated, using T4 DNA ligase, to the DNA fragment including the *Pichia finlandica*-derived (R)-2-octanol dehydrogenase gene excised from pSE-PF01 with the enzymes, to obtain the plasmid pSG-PF01 that can simultaneously express the glucose dehydrogenase and the (R)-2-octanol dehydrogenase. FIG. 9 shows the process of the plasmid construction.

EXAMPLE 25

Construction of Plasmid pSG-PF02 Co-Expressesing (R)-2-octanol Dehydrogenase Gene Derived from Pichia finlandica and Glucose Dehydrogenase Gene Derived from Bacillus subtilis A DNA fragment that includes an (R)-2-octanol dehydrogenase gene derived from *Pichia finlandica* was prepared by digesting pSE-PF02 constructed in Example 16 with two restriction enzymes, EcoRI and SpeI.

Figure 10:
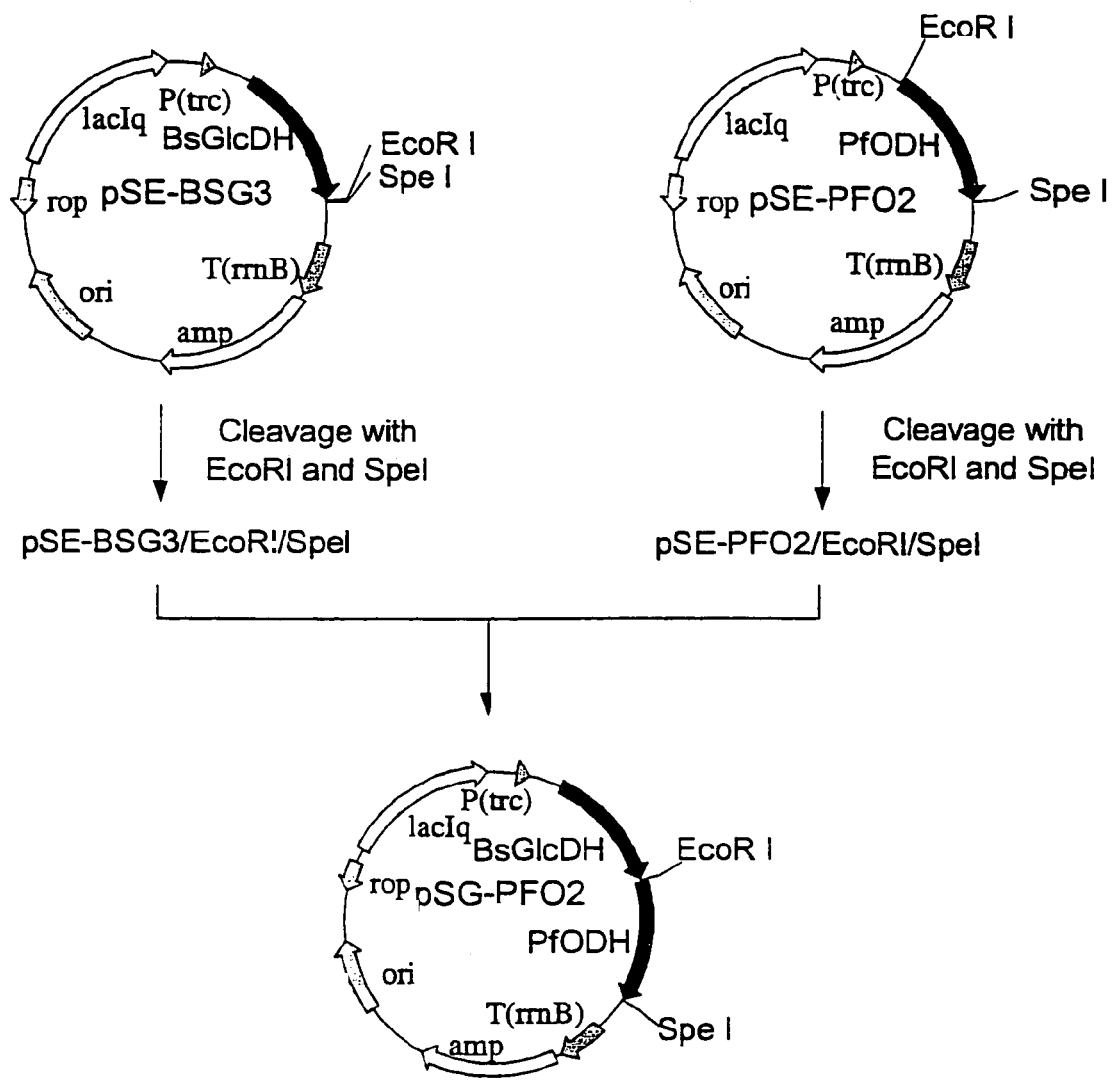
FIG. 10 shows the construction of the plasmid (pSG-PFO2) into which an (R)-2-octanol dehydrogenase gene derived from *Pichia finlandica* and a glucose dehydrogenase gene derived from *Bacillus subtilis* are introduced. In the plasmid map, abbreviations are as follows: P(trc), trc promotor: T(rrnB), rrnBT1T2 terminator; Amp, α-lactamase gene showing ampicillin resistance; ori, replication origin of the plasmid; rop, ROP-protein gene; laqIq, lactose repressor; BsGlcDH, glucose dehydrogenase gene derived from *Bacillus subtilis*; PfODH, (R)-2-octanol dehydrogenase gene derived from *Pichia finlandica*.

The plasmid pSE-BSG3, which was constructed in Example 23 and includes a glucose dehydrogenase gene derived from *Bacillus subtilis*, was digested with two restriction enzymes, EcoRI and SpeI. The fragment was ligated, using T4 DNA ligase, to the DNA fragment including the *Pichia finlandica*-derived (R)-2-octanol dehydrogenase gene excised from pSE-PF02 with the enzymes, to obtain the plasmid pSG-PF02 that can simultaneously express the glucose dehydrogenase and the (R)-2-octanol dehydrogenase. FIG. 10 shows the process of the plasmid construction.

EXAMPLE 26

Simultaneous Expression of Glucose Dehydrogenase Derived From *Bacillus subtilis* and (R)-2-octanol Dehydrogenase Derived From *Pichia finlandica* in *E. coli*

*E. coli* strain JM109 was transformed with the plasmid pSG-PF01 or pSG-PF02 that co-expresses glucose dehydrogenase derived from *Bacillus subtilis* and (R)-2-octanol dehydrogenase derived from *Pichia finlandica*.

Each recombinant *E. coli* was inoculated into liquid LB medium and cultured overnight at 30° C. Then, IPTG was added to 0.1 mM, and the *E. coli* was cultured four hours for more. The two kinds of *E. coli* obtained were collected, and the enzymatic activity was measured.

EXAMPLE 27

Enzymatic Activity of *E. coli* Transformed with pSG-PF01 or pSG-PF02

The transformed *E. coli* in Example 26 (equivalent to 2 mL of the culture) was disrupted by the method of Example 17 to prepare extract. The extract was used for measurement of enzymatic activity. The measurement of glucose dehydrogenase activity was conducted at 30° C. in the reaction solution containing 100 mM potassium phosphate buffer (pH 6.5), 2.5 mM NAD$^+$, 100 mM D-glucose, and the enzyme. 1 U was taken as the amount of the enzyme that catalyzes production of 1 μmol of NADH for 1 minute under the above reaction conditions. Each activity is shown in Table 8.

TABLE 8

| Host ü @ | (R)-2-octanol dehydrogenase activity U/mg-protein |
| --- | --- |
| JM109 | 4.16 |
| HB101 | 8.00 |
| TG1 | 11.0 |
| MG1655 | 10.4 |

EXAMPLE 28

Subcloning of Formate Dehydrogenase Derived From *Mycobacterium vaccae*

The formate dehydrogenase gene was cloned from *Mycobacterium vaccae* described in the reference (Appl. Microbiol. Biotechnol., 44:479–483, 1995) to regenerate reduced form of nicotinamide adenine dinucleotide phosphate.

Figure 11:
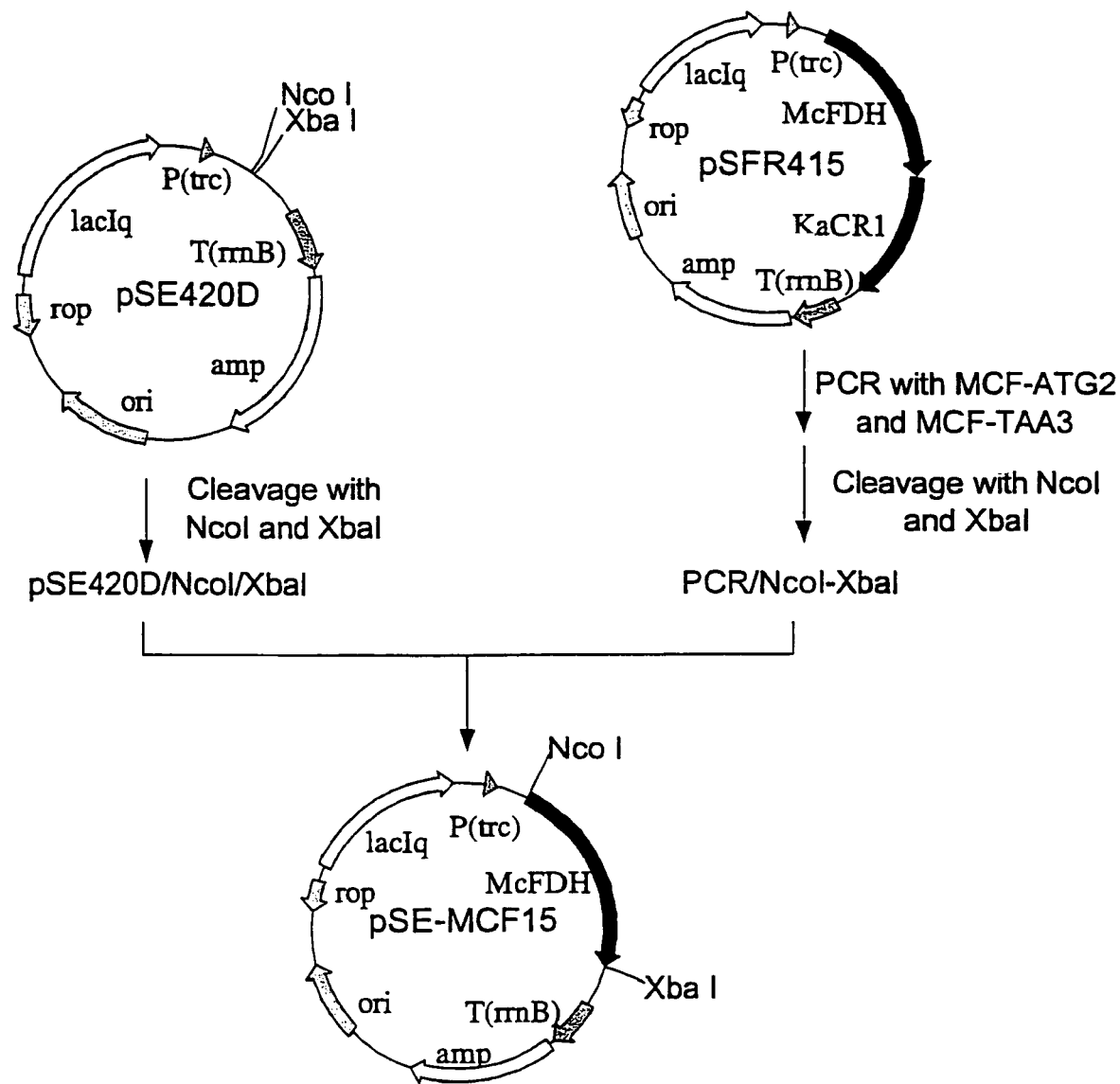
FIG. 11 shows the construction of the plasmid (pSE-MCF15) into which a formate dehydrogenase gene derived from *Mycobacterium vaccae* is introduced. In the plasmid map, abbreviations are as follows: P(trc), trc promotor: T(rrnB), rrnBT1T2 terminator; Amp, β-lactamase gene showing ampicillin resistance; ori, replication origin of the plasmid; rop, ROP-protein gene; laqIq, lactose repressor; McFDH, formate dehydrogenase gene derived from *Mycobacterium vaccae*.

The primers, MCF-ATG2 (SEQ ID NO:19) and MCF-TAA3 (SEQ ID NO:20), were synthesized based on the 5' terminal and 3' terminal nucleotide sequence of the structural gene in the reference to clone only the open reading frame of formate dehydrogenase. PCR was conducted using the plasmid pSFR415 (accession No. 7391 of Seimeikenjouki (FERM BP-7391)) as template for 30 cycles of 95° C. for 45 seconds, 50° C. for 1 minute, and 75° C. for 7 minutes. Then, the specific band was obtained. The obtained DNA fragment was digested with both NcoI and XbaI restriction enzymes. Plasmid vectors pSE420D was also digested with NcoI and XbaI. The DNA fragments digested with the same enzyme were ligated to the vectors with T4 DNA ligase, and pSE-MCF15 was obtained. FIG. 11 shows the process of constructing the plasmid.

As a result of nucleotide sequence analysis of the inserted DNA fragment, the protein encoded by the DNA was identical to the amino acid sequence of the reference.

```
SEQ ID NO: 19: MCF-ATG2
CTTTCTAGAGGAATTCAACCATGGCAAAAGTTCTGTGTGTTC

SEQ ID NO: 20: MCF-TAA3
CAGTCTAGATTAGACCGCTTTTTTGAATTTGGCG
```

International deposit of *E. Coli* strain JM109 transformed with pSFR415:
(a) Name and Address of the depositary institution
   Name: National Institute of Bioscience and Human-Technology, National Institute of Advanced Industrial Science and Technology, Ministry of Economy, Trade, and Industry
   (Previous name: National Institute of Bioscience and Human-Technology,
   Agency of Industrial Science and Technology, Ministry of International Trade and Industry)
   Address: 1-1-3 Higashi, Tsukuba-shi, Ibaragi, 305-8566, Japan
(b) Date of deposit: 10 Nov. 2000
(c) Accession No: FERM BP-7391

EXAMPLE 29

Construction of the Plasmid pSF-PF02 that Expresses Both (R)-2-octanol Dehydrogenase from *Pichia finlandica* and Formate Dehydrogenase Gene from *Mycobacterium* pSE-PFO2 of Example 16 was digested with EcoRI and SpeI, and the DNA fragment including (R)-2-octanol dehydrogenase from *Pichia finlandica* was prepared.

Figure 12:
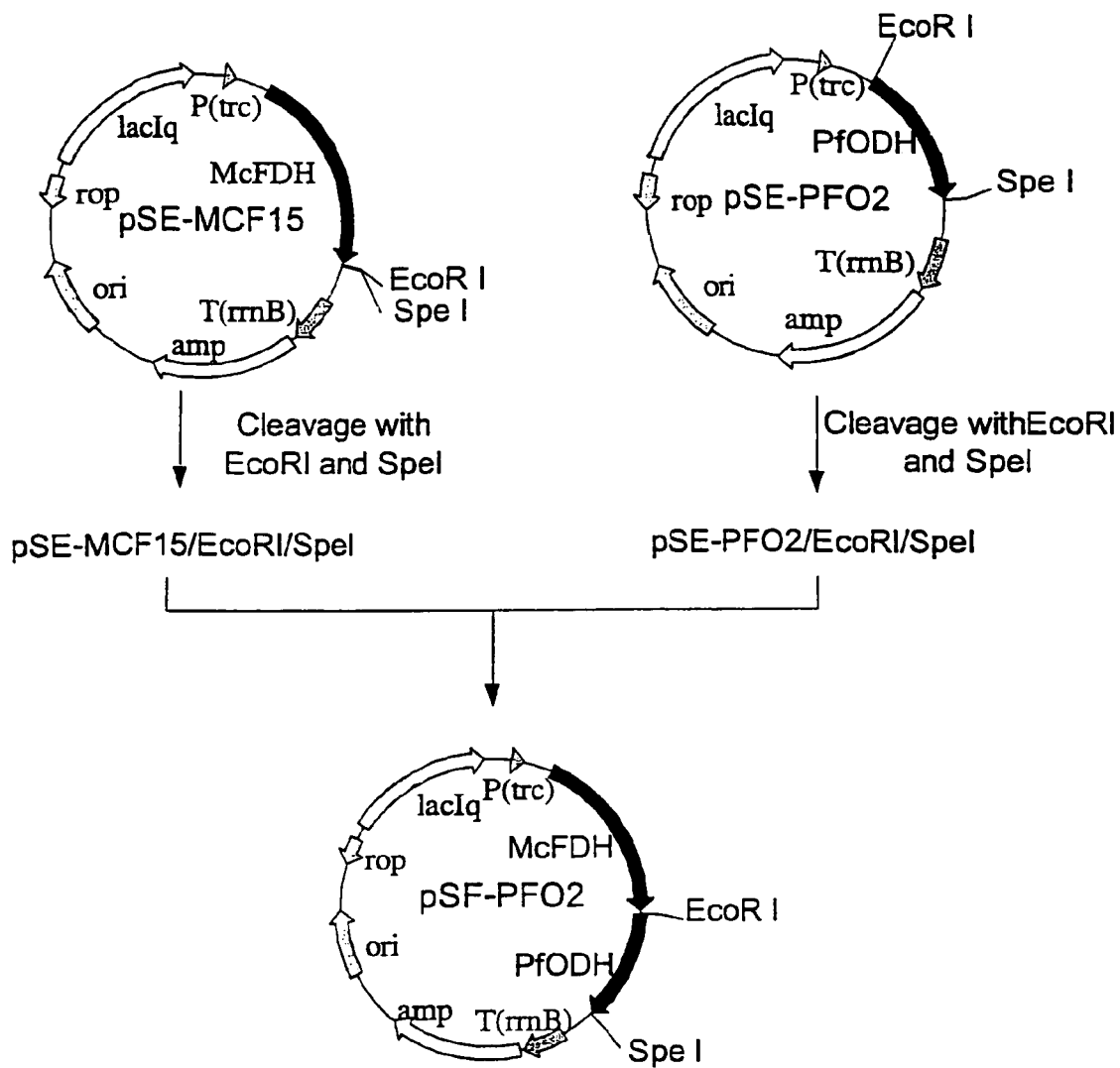
FIG. 12 shows the construction of the plasmid (pSF-PFO2) into which an (R)-2-octanol dehydrogenase gene derived from *Pichia finlandica* and a formate dehydrogenase gene derived from *Mycobacterium vaccae* are introduced. In the plasmid map, abbreviations are as follows: P(trc), trc promotor: T(rrnB), rrnBT1T2 terminator; Amp, β-lactamase gene showing ampicillin resistance; ori, replication origin of the plasmid; rop, ROP-protein gene; laqIq, lactose repressor; McFDH, formate dehydrogenase gene derived from *Mycobacterium vaccae*; PfODH, (R)-2-octanol dehydrogenase gene derived from *Pichia finlandica*.

The plasmid pSE-MCF15 of Example 28 was digested with EcoRI and Spe I, and the DNA fragment including the formate dehydrogenase gene from *Mycobacterium* was prepared. The DNA was ligated to the DNA fragment including (R)-2-octanol dehydrogenase gene from *Pichia finlandica* cutted out from pSE-PFO1 with the same enzyme using T4 DNA ligase. As a result, the plasmid pSF-PF02 that can simultaneously express formate dehydrogenase and (R)-2-octanol dehydrogenase was obtained. FIG. 12 shows the process of constructing the plasmid.

EXAMPLE 30

Simultaneous Expression of (R)-2-octanol Dehydrogenase Derived from *Pichia finlandica* and Formate Dehydrogenase Derived from *Mycobacterium* in *E. coli*

*E. coli* strain JM109 was transformed with the plasmid pSF-PF02 that can co-expresses formate dehydrogenase derived from *Mycobacterium* and (R)-2-octanol dehydrogenase derived from *Pichia finlandica*.

The recombinant *E. coli* was inoculated into liquid LB medium and cultured overnight at 30° C. Then, IPTG was added to 0.1 mM, and the *E. coli* was cultured for more four hours. The *E. coli* obtained was collected, and the enzymatic activity was measured.

EXAMPLE 31

Enzymatic Activity of *E. coli* Transformed with pSF-PF02

The *E. coli* transformed with pSF-PF02 prepared in Example 30 (equivalent to 2 mL of the culture) was disrupted by the method of Example 17 to prepare extract. The extract was used for measurement of enzymatic activity. The measurement of glucose dehydrogenase activity was conducted at 30° C. in the reaction solution containing 100 mM potassium phosphate buffer (pH 6.5), 2.5 mM $NAD^+$, 100 mM formic acid, and the enzyme. 1 U was taken as the amount of the enzyme that catalyzes production of 1 μmol of NADH for 1 minute under the above reaction conditions. The enzymatic activities of the crude enzyme solution obtained from the recombinant *E. coli* were 8.99 U/mg-protein for (R)-2-octanol dehydrogenase activity and 0.653 U/mg-protein for formate dehydrogenase activity.

EXAMPLE 32

Synthesis of (S)-4-chloro-3-hydroxybutyric Acid Ethyl Ester by (R)-2-octanol Dehydrogenase from *Pichia finlandica*

100 mM potassium phosphate buffer (pH 6.5), 139.8 mg NADH, 1.75 U (R)-2-octanol dehydrogenase from *Pichia finlandica* of Example 3, and 0.5% 4-chloroacetoacetic acid ethyl ester were reacted overnight at 30° C. The optical purity of the 4-chloro-3-hydroxybutyric acid ester produced was determined in the following way. The 4-chloro-3-hydroxybutyric acid ester was extracted from the reaction mixture with ethyl acetate, desolvated, and analyzed by liquid chromatography using optical resolution column. The liquid chromatography was conducted using CHIRALCEL OD. (4.6 mm×25 cm) of Daicel Chemical Industries, LTD and the eluate (n-hexane:2-propanol=93:7) at flow rate 1 mL/min, and RI detection was conducted. As a result, 4-chloro-3-hydroxybutyric acid ethyl ester produced by this invention was more than 99% ee of S form.

EXAMPLE 33

Synthesis of 2,3-difluoro-6-nitro[[(R)-2-hydroxypropyl]oxy]benzene by (R)-2-octanol Dehydrogenase from *Pichia finlandica*

1 mL toluene including 1% 2-acetonyloxy-3,4-difluoronitrobenzene was added to 1 mL reaction mixture including 200 mM potassium phosphate buffer (pH 6.5), 86 mM glucose, 1 mM $NAD^+$, 1 mM magnesium sulphate, 1 U (R)-2-octanol dehydrogenase from *Pichia finlandica* of Example 3, and the reaction mixture was reacted at 25° C. for 15 hours with stirrer.

As a result of the analysis of the final reaction mixture, 1.0 g/L of 2,3-difluoro-6-nitro-[[(R)-2-hydroxypropyl]oxy]-benzene was produced, and its optical purity was about 100%.

Quantitative determination of 2,3-difluoro-6-nitro-[[(R)-2-hydroxypropyl]oxy]-benzene was done by HPLC analysis of the product contained in aqueous phase and organic phase with eluate (water/acetonitrile=1/1) at flow rate 0.5 mL/min at room temperature. The UV detection was done at 260 nm.

The measurement of optical purity of 2,3-difluoro-6-nitro-[[(R)-2-hydroxypropyl]oxy]-benzene was conducted by HPLC analysis using optical resolution column (CHIRALCEL OD. 0.46×25 cm, Daicel Chemical Industries, LTD) with the eluate (hexane/2-propanol=9/1) at flow rate 1 mL/min at 40° C. The UV detection was done at 260 nm.

EXAMPLE 34

Synthesis of 2,3-difluoro-6-nitro[[(R)-2-hydroxypropyl]oxy]benzene Using pSF-PFO2

The *E. Coli* transformed with pSF-PF02 of Example 30 (corresponding 5 mL culture medium) was collected. 500 mg 2-acetonyloxy-3,4-difluoronitrobenzene was added to 5.22 mL reaction mixture including 500 mM HEPES/NaOH buffer (pH 6.5), 829 mM sodium formate, and 1 mM magnesium sulphate, and the reaction mixture was reacted at 30° C. for 18 hours with stirrer.

As a result of the analysis of the final reaction mixture, 486 mg of 2,3-difluoro-6-nitro-[[(R)-2-hydroxypropyl]oxy]-benzene was produced, and its optical purity was about 100%.

Quantitative determination of 2,3-difluoro-6-nitro-[[(R)-2-hydroxypropyl]oxy]-benzene was done in the following way: The product was extracted by addition of toluene to the reaction mixture, and the product contained in aqueous phase and organic phase was determined by gas chromatography. The yield to the synthon was obtained. The condition of the gas chromatography was as follows: OV-210 20% Chromosorb W (AW-DMCS) 60/80 mesh (G-L Science, 3.2 mm×200 cm) at 170° C. of column temperature. The detection was done using flame ionization detector (FID).

The measurement of optical purity of 2,3-difluoro-6-nitro-[[(R)-2-hydroxypropyl]oxy]-benzene was conducted by HPLC analysis using optical resolution column (CHIRALCEL OD. 0.46×25 cm, Daicel Chemical Industries, LTD) with the eluate (hexane/ethanol=9/1) at flow rate 1 mL/min at 40° C. of column temperature. The UV detection was done at 260 nm.

EXAMPLE 35

Purification of (R)-2-octanol Dehydrogenase From *Candida utilis*

*Candida utilis* IFO 0988 strain was cultured in 3.6 L of medium B and the microbial cells were prepared by centrifugation. Obtained microbial cells were suspended in 100 mM potassium phosphate buffer (pH 8.0), 10% glycerol, 1 mM ethylenediaminetetraacetic acid 2Na (EDTA·2Na), 0.01% 2-mercaptoethanol, and 2 mM phenyl methane sulfonylfluoride (PMSF) and homogenized with bead beater (Biospec). After that, microbial cell debris were removed by centrifugation and cell-free extract was obtained. Protamine sulphate was added to this cell-free extract, and supernatant was obtained by centrifugation to remove nucleic acid. Ammonium sulfate was added to the supernatant, and the supernatant which was crude enzymatic solution was obtained in 30% saturation. The solution was dialyzed with standard buffer including 30% saturated ammonium and added to phenyl-sepharose HP (2.6 cm×10 cm) equilibrated with the same buffer. The gradient elution was conducted with 30% to 0% saturated ammonium sulfate. The fraction having selectivity of (R)-2-octanol among extracted fractions was recovered and concentrated by ultrafiltration. Composition of medium B used are followings:

Medium B:
  10 g/L yeast extract
  20 g/L peptone
  1% methanol
  pH 6.0

After the enzyme solution concentrated was dialyzed with the standard buffer, it was added to Blue-Sepharose HP (1.6 cm×2.5 cm) and washed with the buffer. Then, the concentration gradient elution with 0 to 1.5 M sodium chloride was conducted. As the activity of (R)-2-octanol dehydrogenase was eluted in the part of fraction passed through, this fraction was recovered and concentrated. After the enzyme solution was added to Mono Q HR 5/5 (0.5 cm×5 cm) which is equilibrated with the standard buffer and washed with the buffer, the concentration gradient elution with 0 to 1 M sodium chloride was conducted. As the activity of (R)-2-octanol dehydrogenase was eluted in the part of gradient elution, this fraction was recovered and concentrated. Gel filtration of the concentrated enzymatic solution was conducted using Superdex 200 (0.32 cm×30 cm) with standard buffer including 0.3 M sodium chloride. The enzyme was obtained by concentrating the active fraction.

The specific activity of the enzyme was about 3.33 U/mg which is the activity of oxidizing (R)-2-octanol. Summary of the purification is shown in Table 9.

TABLE 9

| Step | Amount of Protein (mg) | Total activity (U) | Specific activity (U/mg) |
| --- | --- | --- | --- |
| Cell-free extract | 1,220 | 6.58 | 0.00539 |
| Nucleic acid removal | 396 | 2.30 | 0.00581 |
| Ammonium Sulfate 30% | 471 | 1.14 | 0.00242 |
| Phenyl-Sepharose | 17.7 | 0.757 | 0.0429 |
| Blue-Sepharose | 10.2 | 0.745 | 0.0727 |
| MonoQ | 0.776 | 0.386 | 0.497 |
| Superdex 200 | 0.0131 | 0.0434 | 3.33 |

EXAMPLE 36

Measuring Molecular Weight of (R)-2-octanol Dehydrogenase

The molecular weight of the enzyme of Example 35 from *Candida utilis* was about 150,000 Da when it was measured using gel filtration column of Superdex 200.

EXAMPLE 37

Optimum pH of (R)-2-octanol Dehydrogenase

Figure 13:
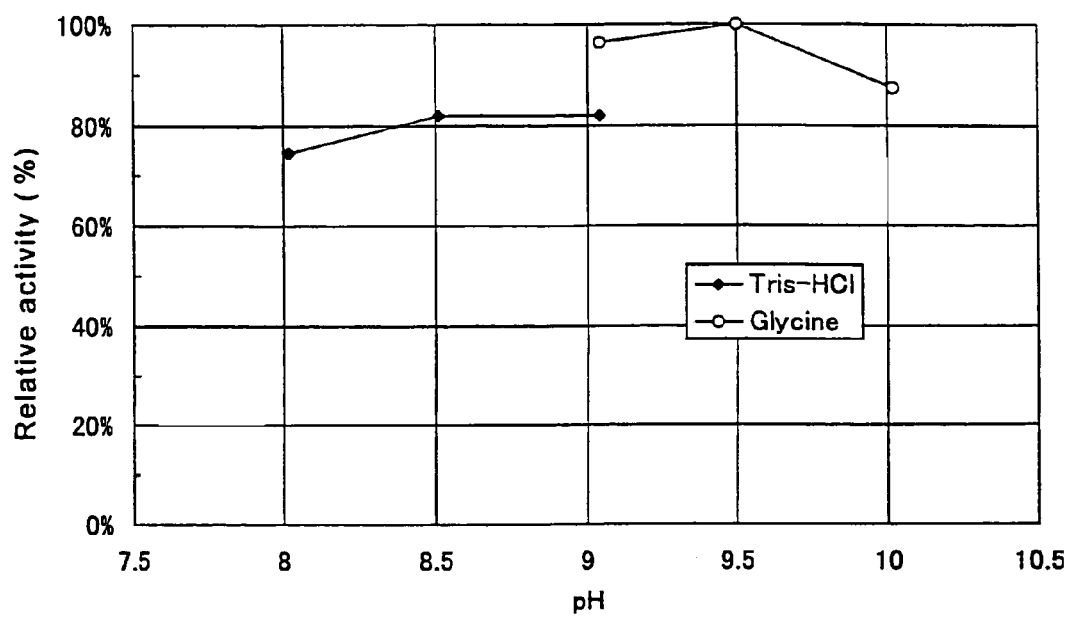
FIG. 13 shows the effect of pH change on the enzymatic activity of (R)-2-octanol dehydrogenase purified from *Candida utilis*. The longitudinal axis indicates relative activity with taking the maximal activity as 100.

We examined (R)-2-octanol dehydrogenase activity of the enzyme obtained from Example 35 changing pH by using Tris-HCl buffer and, Glycine buffer. FIG. 13 shows relative activity with taking the maximal activity as 100. As a result, the optimum pH of the enzyme was from 8.5 to 11.0.

Figure 14:
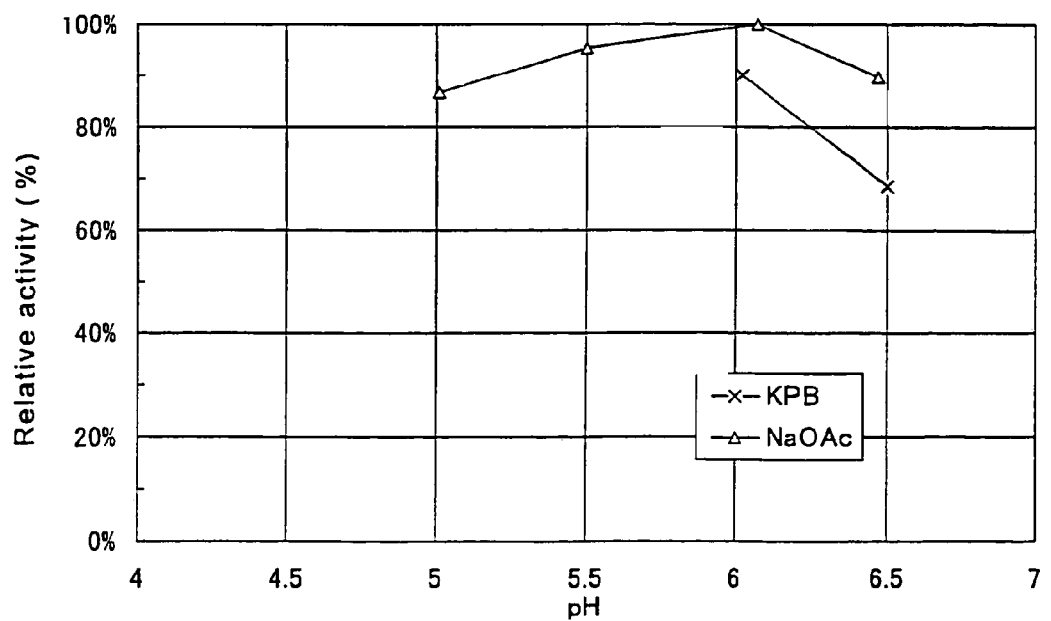
FIG. 14 shows the effect of pH change on the ethyl 4-chloroacetoacetate-reducing activity of (R)-2-octanol dehydrogenase purified from *Candida utilis*. The longitudinal axis indicates relative activity with taking the maximal activity as 100.

We also examined 4-chloroacetoacetic acid ethyl ester reductase activity of the enzyme obtained from Example 35 changing pH by using phosphate buffer (KPB), sodium acetate (NaOAc). FIG. 14 shows relative activity with taking the maximal activity as 100. As a result, the optimum pH of the enzyme was from 5.0 to 6.5.

EXAMPLE 38

Substrate Specificity of (R)-2-octanol Dehydrogenase

The (R)-2-octanol dehydrogenase was reacted with various alcohols and its oxidation activity was measured. Table 10 shows relative activities with taking the oxidation activity of the (R)-2-octanol as 100 using $NAD^+$ as a coenzyme. As a result, the relative activity was 6.7% for (S)-2-octanol, 8.3% for 2-propanol, and 86% for (R)-1-phenylethanol.

TABLE 10

| Substrate (oxidation reaction) | |
| --- | --- |
| (R)-2-octanol | 100 |
| (S)-2-octanol | 6.7 |
| 2-octanol | 8.3 |
| (R)-1-phenylethanol | 86.7 |
| (S)-1-phenylethanol | 6.7 |

The enzyme of Example 35 was also reacted with various ketones and its reduction activity was measured. Table 11 shows relative activities with taking the reduction activity of the 4-chloroacetoacetic acid ethyl ester as 100 using NADH as a coenzyme. As a result, the relative activity was 26.6% for 2-octanone and 25.3% for acetophenone.

TABLE 11

| Substrate (oxidation reaction) | |
| --- | --- |
| Ethyl 4-chloroacetoacetate | 100 |
| 2-Octanone | 26.6 |
| Acetophenone | 25.3 |

EXAMPLE 39

Synthesis of (S)-4-chloro-3-hydroxybutyric Acid Ethyl Ester by (R)-2-octanol Dehydrogenase from *Candida utilis*

100 mM potassium phosphate buffer (pH 6.5), 139.8 mg NADH, 0.06 U (R)-2-octanol dehydrogenase from *Candida utilis*, and 0.5% 4-chloroacetoacetic acid ethyl ester were reacted overnight at 30° C. The optical purity of the 4-chloro-3-hydroxybutyric acid ethyl ester produced was determined in the same way as Example 32. As a result, 4-chloro-3-hydroxybutyric acid ethyl ester produced by this invention was more than 97% ee of S form.

INDUSTRIAL APPLICABILITY

The present invention provides NADH-dependent (R)-2-octanol dehydrogenase that is advantageous for industrial production. Efficient production of optically active alcohols such as (S)-4-halo-3-hydroxybutyric acid esters becomes possible using this enzyme. Especially, (S)-4-halo-3-hydroxybutyric acid esters, which can be obtained by the enzymatic reaction based on this invention using 4-haloacetoacetic acid esters as substrates, are intermediates in synthesizing medicines and pesticides such as HMG-CoA reductase inhibitors, D-carnitine, etc. Therefore, the present invention is industrially very useful.

Above all, (R)-propoxybenzene derivatives described in JP-A Hei 02-732 are useful compounds as intermediates such as optically active substances of ofloxacin ((S)-(−)-9-fluoro-3-methyl-10-(4-methyl-1-piperazinyl)-7-oxo-2,3-dihydro-7H-pyrido[1,2,3-de][1,4]benzooxazine-6-carboxylic acid, JP-A Sho 62-252790), which are synthetic antibacterial drugs. It has confirmed that the specific optical isomer of ofloxacin has high antibacterial activity. The present invention enables obtaining, with high optical purity, intermediates in synthesizing ofloxacin and therefore contributes to the synthesis of optical isomer of ofloxacin.

What is claimed is:

1. A method for producing an (S)-4-halo-3-hydroxybutyric acid ester derivative, the method comprising reacting an (R)-2-octanol dehydrogenase having a molecular weight of about 30,000 Da as determined by SDS-PAGE and about 83,000 Da as determined by gel filtration, or a microorganism producing the (R)-2-octanol dehydrogenase, with a 4-haloacetoacetic acid ester derivative to reduce the 4-haloacetoacetic acid ester derivative, wherein the (R)-2-octanol dehydrogenase is a polypeptide chosen from (a) or (b) below:
   (a) polypeptide comprising an amino acid sequence at least 95% identical to the amino acid sequence of SEQ ID NO:2; or
   (b) a polypeptide comprising the amino acid sequence of SEQ ID NO:2.

2. The method of claim 1, wherein the microorganism is a transformant comprising a recombinant vector into which a polynucleotide encoding the (R)-2-octanol dehydrogenase is inserted.

3. The method of claim 1, wherein the 4-haloacetoacetic acid ester derivative is 4-chloroacetoacetic acid ethyl ester and wherein the (S)-4-halo-3-hydroxybutyric acid ester derivative is (S)-4-chloro-3-hydroxybutyric acid ethyl ester.

4. The method of claim 1, the method further comprising converting an oxidized form of β-nicotinamide adenine dinucleotide into a reduced form thereof.

5. The method of claim 1, wherein the (R)-2-octanol dehydrogenase has an optimal pH for the reduction reaction in a range from 5.0 to 6.5.

6. The method of claim 1, wherein the reacting step is carried out with the microorganism producing the (R)-2-octanol dehydrogenase, and said microorganism belongs to the genus Candida or the genus Ogataea.

7. The method of claim 1, wherein the reacting step is carried out with the microorganism producing the (R)-2-octanol dehydrogenase, and the microorganism belongs to the genus Pichia.

8. The method of claim 1, wherein the (R)-2-octanol dehydrogenase is at least 75% pure, has been treated with an organic solvent or is in a cell-free extract.

9. The method of claim 1, further comprising using a reduced form of β-nicotinamide adenine dinucleotide (NADH) as a coenzyme.

10. The method of claim 1, wherein the (R)-2-octanol dehydrogenase comprises an amino acid sequence at least 95% identical to the amino acid sequence of SEQ ID NO:2.

11. The method of claim 1, wherein the (R)-2-octanol dehydrogenase comprises the amino acid sequence of SEQ ID NO:2.

12. The method of claim 1, wherein the (R)-2-octanol dehydrogenase consists of the amino acid sequence of SEQ ID NO:2.

13. A method for producing an (S)-4-halo-3-hydroxybutyric acid ester derivative, the method comprising reacting (i) an (R)-2-octanol dehydrogenase, or a microorganism producing the (R)-2-octanol dehydrogenase, with (ii) a 4-haloacetoacetic acid ester derivative to reduce the 4-haloacetoacetic acid ester derivative, wherein the (R)-2-octanol dehydrogenase oxidizes the S form of (R)-2-octanol with an activity of 50 or less when taking the activity on R form as 100, wherein the (R)-2-octanol dehydrogenase is a polypeptide chosen from (a) or (b) below:
   (a) a polypeptide comprising an amino acid sequence at least 95% identical to the amino acid sequence of SEQ ID NO:2; or
   (b) a polypeptide comprising the amino acid sequence of SEQ ID NO:2.

14. The method of claim 13, wherein the (R)-2-octanol dehydrogenase is obtained from *Pichia*, or a transformant comprising a recombinant vector into which a polynucleotide encoding the (R)-2-octanol dehydrogenase from *Pichia* is inserted.

15. A method for producing an (S)-4-halo-3-hydroxybutyric acid ester derivative, the method comprising reacting an (R)-2-octanol.dehydrogenase having a molecular weight of about 30,000 Da as determined by SDS-PAGE and about 83,000 Da as determined by gel filtration, or a microorganism producing the (R)-2-octanol dehydrogenase, with a 4-haloacetoacetic acid ester derivative to reduce the 4-haloacetoacetic acid ester derivative, wherein the (R)-2-octanol dehydrogenase is a polypeptide chosen from (a) or (c) below:
 (a) a polypeptide encoded by a polynucleotide that hybridizes under stringent conditions with a nucleic acid probe consisting of the complement of the nucleotide sequence of SEQ ID NO:1, wherein the stringent conditions comprise washing in 0.2×SSC in 0.1% SDS at 65° C.;
 (b) a polypeptide comprising an amino acid sequence that is a variant of SEQ ID NO:2 with up to 30 conservative amino acid substitutions; or
 (c) a polypeptide comprising an amino acid sequence that is a variant of SEQ ID NO:2 with up to 10 conservative amino acid substitutions.

16. The method of claim 15, wherein the (R)-2-octanol dehydrogenase is encoded by a polynucleotide that hybridizes under stringent conditions with a nucleic acid probe consisting of the complement of the nucleotide sequence of SEQ ID NO:1, wherein the stringent conditions comprise washing in 0.2×SSC in 0.1% SDS at 65° C.

17. The method of claim 15, wherein the (R)-2-octanol dehydrogenase comprises an amino acid sequence that is a variant of SEQ ID NO:2 with up to 30 conservative amino acid substitutions.

18. The method of claim 15, wherein the (R)-2-octanol dehydrogenase comprises an amino acid sequence that is a variant of SEQ ID NO:2 with up to 10 conservative amino acid substitutions.

19. A method for producing an (S)-4-halo-3-hydroxybutyric acid ester derivative, the method comprising reacting (i) an (R)-2-octanol dehydrogenase, or a microorganism producing the (R)-2-octanol dehydrogenase, with (ii) a 4-haloacetoacetic acid ester derivative to reduce the 4-haloacetoacetic acid ester derivative, wherein the (R)-2-octanol dehydrogenase oxidizes the S form of (R)-2-octanol with an activity of 50 or less when taking the activity on R form as 100, wherein the (R)-2-octanol dehydrogenase is a polypeptide chosen from (a) or (c) below:
 (a) a polypeptide encoded by a polynucleotide that hybridizes under stringent conditions with a nucleic acid probe consisting of the complement of the nucleotide sequence of SEQ ID NO:1, wherein the stringent conditions comprise washing in 0.2×SSC in 0.1% SDS at 65° C.;
 (b) a polypeptide comprising an amino acid sequence that is a variant of SEQ ID NO:2 with up to 30 conservative amino acid substitutions; or
 (c) a polypeptide comprising an amino acid sequence that is a variant of SEQ ID NO:2 with up to 10 conservative amino acid substitutions.

20. The method of claim 14, wherein the *Pichia* is *Pichia finlandica*.

21. The method of claim 19, wherein the (R)-2-octanol dehydrogenase is obtained from *Pichia*, or a transformant comprising a recombinant vector into which a polynucleotide encoding the (R)-2-octanol dehydrogenase from *Pichia* is inserted.

22. The method of claim 21, wherein the *Pichia* is *Pichia finlandica*.

* * * * *

UNITED STATES PATENT AND TRADEMARK OFFICE
CERTIFICATE OF CORRECTION

| | | |
|---|---|---|
| PATENT NO. | : 7,202,069 B2 | Page 1 of 1 |
| APPLICATION NO. | : 10/766421 | |
| DATED | : April 10, 2007 | |
| INVENTOR(S) | : Masatake Kudoh and Hiroaki Yamamoto | |

It is certified that error appears in the above-identified patent and that said Letters Patent is hereby corrected as shown below:

Column 14, line 2,
    Delete, "for *Streptomyces lividans*, pU486 (Mol. Gen."
    and insert -- for *Streptomyces lividans,* pIJ486 (Mol. Gen. --

Column 26, line 51,
    Delete "primer, 10 mmol dNTP" and insert -- primer, 10 nmol dNTP --

Column 47, line 44,
    Delete "(a) polypeptide comprising" and insert -- (a) a polypeptide comprising --

Column 48, line 49,
    Delete "The method of claim 1" and insert -- The method of claim 11 --

Column 50, line 20,
    Delete "at 65° C.;" and insert -- at 65° C; --

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 20

<210> SEQ ID NO 1
<211> LENGTH: 765
<212> TYPE: DNA
<213> ORGANISM: Pichia finlandica
<220> FEATURE:
<221> NAME/KEY: CDS
<222> LOCATION: (1)...(762)

<400> SEQUENCE: 1

```
atg tct tat aac ttc cat aac aag gtt gca gtt gtt act gga gct cta     48
Met Ser Tyr Asn Phe His Asn Lys Val Ala Val Val Thr Gly Ala Leu
1               5                   10                  15 tca gga atc ggc tta agc gtc gca aaa aag ttc ctt cag ctc ggc gcc     96
Ser Gly Ile Gly Leu Ser Val Ala Lys Lys Phe Leu Gln Leu Gly Ala
            20                  25                  30 aaa gta acg atc tct gat gtc agt gga gag aaa aaa tat cac gag act    144
Lys Val Thr Ile Ser Asp Val Ser Gly Glu Lys Lys Tyr His Glu Thr
        35                  40                  45 gtt gtt gct ctg aaa gcc caa aat ctc aac act gac aac ctc cat tat    192
Val Val Ala Leu Lys Ala Gln Asn Leu Asn Thr Asp Asn Leu His Tyr
    50                  55                  60 gta cag gca gat tcc agc aaa gaa gaa gat aac aag aaa ttg att tcg    240
Val Gln Ala Asp Ser Ser Lys Glu Glu Asp Asn Lys Lys Leu Ile Ser
65                  70                  75                  80 gaa act ctg gca acc ttt ggg ggc ctg gat att gtt tgt gct aat gca    288
Glu Thr Leu Ala Thr Phe Gly Gly Leu Asp Ile Val Cys Ala Asn Ala
                85                  90                  95 gga att gga aag ttc gct ccc acc cat gaa aca ccc ttc gac gta tgg    336
Gly Ile Gly Lys Phe Ala Pro Thr His Glu Thr Pro Phe Asp Val Trp
            100                 105                 110 aag aag gtg att gct gtg aat ttg aat gga gta ttc tta ctg gat aag    384
Lys Lys Val Ile Ala Val Asn Leu Asn Gly Val Phe Leu Leu Asp Lys
        115                 120                 125 cta gcc atc aat tac tgg cta gag aaa agc aaa ccc ggc gta att gtc    432
Leu Ala Ile Asn Tyr Trp Leu Glu Lys Ser Lys Pro Gly Val Ile Val
    130                 135                 140 aac atg gga tca gtc cac tct ttt gta gca gct cct ggc ctt gcg cat    480
Asn Met Gly Ser Val His Ser Phe Val Ala Ala Pro Gly Leu Ala His
145                 150                 155                 160 tat gga gct gca aaa ggc ggt gtc aaa ctg tta aca caa aca ttg gct    528
Tyr Gly Ala Ala Lys Gly Gly Val Lys Leu Leu Thr Gln Thr Leu Ala
                165                 170                 175 cta gag tac gca tct cat ggt att aga gta aat tct gtc aat ccg ggg    576
Leu Glu Tyr Ala Ser His Gly Ile Arg Val Asn Ser Val Asn Pro Gly
            180                 185                 190 tac att tcg act cct ttg ata gat gag gtt ccg aaa gag cgg ttg gat    624
Tyr Ile Ser Thr Pro Leu Ile Asp Glu Val Pro Lys Glu Arg Leu Asp
        195                 200                 205 aaa ctt gta agc ttg cac cct att ggg aga cta ggt cgt cca gag gaa    672
```

```
Lys Leu Val Ser Leu His Pro Ile Gly Arg Leu Gly Arg Pro Glu Glu
        210                 215                 220 gtt gct gat gca gtc gca ttt ctg tgt tcc cag gag gcc act ttc atc      720
Val Ala Asp Ala Val Ala Phe Leu Cys Ser Gln Glu Ala Thr Phe Ile
225                 230                 235                 240 aac ggc gtt tct ttg ccg gtt gac ggg ggg tac aca gcc cag taa          765
Asn Gly Val Ser Leu Pro Val Asp Gly Gly Tyr Thr Ala Gln
                245                 250

<210> SEQ ID NO 2
<211> LENGTH: 254
<212> TYPE: PRT
<213> ORGANISM: Pichia finlandica

<400> SEQUENCE: 2

Met Ser Tyr Asn Phe His Asn Lys Val Ala Val Thr Gly Ala Leu
 1               5                  10                  15

Ser Gly Ile Gly Leu Ser Val Ala Lys Lys Phe Leu Gln Leu Gly Ala
                20                  25                  30

Lys Val Thr Ile Ser Asp Val Ser Gly Glu Lys Lys Tyr His Glu Thr
            35                  40                  45

Val Val Ala Leu Lys Ala Gln Asn Leu Asn Thr Asp Asn Leu His Tyr
        50                  55                  60

Val Gln Ala Asp Ser Ser Lys Glu Glu Asp Asn Lys Lys Leu Ile Ser
65                  70                  75                  80

Glu Thr Leu Ala Thr Phe Gly Gly Leu Asp Ile Val Cys Ala Asn Ala
                85                  90                  95

Gly Ile Gly Lys Phe Ala Pro Thr His Glu Thr Pro Phe Asp Val Trp
            100                 105                 110

Lys Lys Val Ile Ala Val Asn Leu Asn Gly Val Phe Leu Leu Asp Lys
        115                 120                 125

Leu Ala Ile Asn Tyr Trp Leu Glu Lys Ser Lys Pro Gly Val Ile Val
    130                 135                 140

Asn Met Gly Ser Val His Ser Phe Val Ala Ala Pro Gly Leu Ala His
145                 150                 155                 160

Tyr Gly Ala Ala Lys Gly Gly Val Lys Leu Leu Thr Gln Thr Leu Ala
                165                 170                 175

Leu Glu Tyr Ala Ser His Gly Ile Arg Val Asn Ser Val Asn Pro Gly
            180                 185                 190

Tyr Ile Ser Thr Pro Leu Ile Asp Glu Val Pro Lys Glu Arg Leu Asp
        195                 200                 205

Lys Leu Val Ser Leu His Pro Ile Gly Arg Leu Gly Arg Pro Glu Glu
    210                 215                 220

Val Ala Asp Ala Val Ala Phe Leu Cys Ser Gln Glu Ala Thr Phe Ile
225                 230                 235                 240

Asn Gly Val Ser Leu Pro Val Asp Gly Gly Tyr Thr Ala Gln
                245                 250

<210> SEQ ID NO 3
<211> LENGTH: 10
<212> TYPE: PRT
<213> ORGANISM: Pichia finlandica

<400> SEQUENCE: 3

Val Ala Val Val Thr Gly Ala Leu Ser Gly
 1               5                  10
```

```
<210> SEQ ID NO 4
<211> LENGTH: 12
<212> TYPE: PRT
<213> ORGANISM: Pichia finlandica

<400> SEQUENCE: 4

Leu Ile Ser Glu Thr Leu Ala Thr Phe Gly Gly Leu
 1               5                  10

<210> SEQ ID NO 5
<211> LENGTH: 10
<212> TYPE: PRT
<213> ORGANISM: Pichia finlandica

<400> SEQUENCE: 5

Leu Gly Arg Pro Glu Glu Val Ala Asp Ala
 1               5                  10

<210> SEQ ID NO 6
<211> LENGTH: 29
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: (1)...(9)
<223> OTHER INFORMATION: BamHI site

<400> SEQUENCE: 6
gtcggatccg tbgchgtbgt bachgghgc                                29

<210> SEQ ID NO 7
<211> LENGTH: 29
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: (1)...(9)
<223> OTHER INFORMATION: BamHI site
<220> FEATURE:
<221> NAME/KEY: misc_feature
<222> LOCATION: 15, 18, 27
<223> OTHER INFORMATION: n = a, c, t or g

<400> SEQUENCE: 7
gtcggatccg crtcngcnac ytcytcngg                                29

<210> SEQ ID NO 8
<211> LENGTH: 623
<212> TYPE: DNA
<213> ORGANISM: Pichia finlandica

<400> SEQUENCE: 8
gctctatcag gaatcggctt aagcgtcgca aaaaagttcc ttcagctcgg cgccaaagta      60
acgatctctg atgtcagtgg agagaaaaaa tatcacgaga ctgttgttgc tctgaaagcc    120
caaaatctca acactgacaa cctccattat gtacaggcag attccagcaa agaagaagat    180
aacaagaaat tgatttcgga aactctggca acctttgggg gcctggatat tgtttgtgct    240
aatgcaggaa ttggaaagtt cgctcccacc catgaaacac ccttcgacgt atggaagaag    300
gtgattgctg tgaatttgaa tgagtattc ttactggata agctagccat caattactgg    360
ctagagaaaa gcaaacccgg cgtaattgtc aacatgggat cagtccactc ttttgtagca    420
```

```
gctcctggcc ttgcgcatta tggagctgca aaaggcggtg tcaaactgtt aacacaaaca      480
ttggctctag agtacgcatc tcatggtatt agagtaaatt ctgtcaatcc ggggtacatt      540
tcgactcctt tgatagatga ggttccgaaa gagcggttgg ataaacttgt aagcttgcac      600
cctattggga gactaggtcg tcc                                              623
```

<210> SEQ ID NO 9
<211> LENGTH: 29
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: (1)...(9)
<223> OTHER INFORMATION: BamHI site

<400> SEQUENCE: 9

```
gtcggatcct cagagatcgt tactttggc                                         29
```

<210> SEQ ID NO 10
<211> LENGTH: 29
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: (1)...(9)
<223> OTHER INFORMATION: BamHI site

<400> SEQUENCE: 10

```
gtcggatccc gactcctttg atagatgag                                         29
```

<210> SEQ ID NO 11
<211> LENGTH: 599
<212> TYPE: DNA
<213> ORGANISM: Pichia finlandica

<400> SEQUENCE: 11

```
tgggctgaac ctggctgtgc tactgggcag agcaaaatca gatagaagag cttgtgtttt       60
tgtagcaccc ctctttttttt ttgaaattct ctacagctca attacctgtt cacattcaat     120
acagagtact atcttttcga tttcttatca gataagcaat tgacaatatt agtagcacct     180
gatgcacttt tcgagaacac acctgagtac aaaacaatat atatcattat attagaacag     240
tgacattgag aacaattttc cagcatataa tgtaattagg tgcatcaaca accaggaaaa     300
acacctgatt aaaaaatccg gatattaaga atcatgaaac aaaattcaat gttaccctac     360
ccattccttc tcggaacctc ctgatgactt attaatagtg aggttgttcc gataaaaatc     420
gcgaatttct ccattccata aattctccta taacttggct tactatacac acacactatt     480
atcgatatgt cttataactt ccataacaag gttgcagttg ttactggagc tctatcagga     540
atcggcttaa gcgtcgcaaa aaagttcctt cagctcggcg ccaaagtaac gatctctga     599
```

<210> SEQ ID NO 12
<211> LENGTH: 581
<212> TYPE: DNA
<213> ORGANISM: Pichia finlandica

<400> SEQUENCE: 12

```
cgactccttt gatagatgag gttccgaaag agcggttgga taaacttgta agcttgcacc       60
ctattgggag actaggtcgt ccagaggaag ttgctgatgc agtcgcattt ctgtgttccc     120
```

-continued

```
aggaggccac tttcatcaac ggcgtttctt tgccggttga cggggggtac acagcccagt      180
aaattggaca cttttttgctc tttattatct tccccgcgtt tcaccaatta tccggtgtac      240
gtaggttgca gtgactttct ggtttctgca cttgaatgaa actctctttt accccacaaa      300
atcagctcag taaattatct tgtgtatata taaataagac agaaaccctg tggactccta      360
gtatggtgtt ctactttcat taaggcagtc acaaaagcaa tggcgaaatc aactgatgga      420
aagatagtta cactggagga gcaggcctac aatggcccac ccgcacggat cataggagaa      480
gctatcgcca ttaaagcgaa gctggctgcc aatcggacac tcccagttaa gtttgaaaga      540
aagcgtggtc ttcaaccacc accagggatg tctagacaag a                          581
```

<210> SEQ ID NO 13
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 13

```
tcgacatgtc ttataatttc cataacaag                                         29
```

<210> SEQ ID NO 14
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 14

```
gcagaattcc tctagattac tgggctgtgt accc                                   34
```

<210> SEQ ID NO 15
<211> LENGTH: 37
<212> TYPE: DNA
<213> ORGANISM: Artificial Sequence
<220> FEATURE:
<223> OTHER INFORMATION: Artificially synthesized primer sequence

<400> SEQUENCE: 15

```
cacgaattct aaaatgtctt ataatttcca taacaag                                37
```

<210> SEQ ID NO 16
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 16

```
agtactagta ttactgggct gtgtaccc                                          28
```

<210> SEQ ID NO 17
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 17

```
agaccatgga tccaatgtat ccagatttaa aaggaa                                 36
```

<210> SEQ ID NO 18

```
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 18
gaatctagat taaccgcggc ctgcctg                                          27

<210> SEQ ID NO 19
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 19
ctttctagag gaattcaacc atggcaaaag ttctgtgtgt tc                         42

<210> SEQ ID NO 20
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 20
cagtctagat tagaccgctt ttttgaattt ggcg                                  34
```